United States Patent
Schempf et al.

(10) Patent No.: US 6,917,176 B2
(45) Date of Patent: Jul. 12, 2005

(54) GAS MAIN ROBOTIC INSPECTION SYSTEM

(75) Inventors: Hagen Schempf, Pittsburgh, PA (US); Edward Mutschler, Wexford, PA (US); Vitaly Goltsberg, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 0 days.

(21) Appl. No.: 10/094,353

(22) Filed: Mar. 7, 2002

(65) Prior Publication Data

US 2002/0190682 A1 Dec. 19, 2002

Related U.S. Application Data

(60) Provisional application No. 60/273,845, filed on Mar. 7, 2001.

(51) Int. Cl.$^7$ .................................................. B25J 9/18
(52) U.S. Cl. ........................... 318/568.11; 318/568.12; 318/568.16; 700/258; 700/259; 901/44
(58) Field of Search ................... 318/568.11, 568.12, 318/568.16; 700/258, 259; 901/44; 464/4, 106, 113; 180/901

(56) References Cited

U.S. PATENT DOCUMENTS

| | | | |
|---|---|---|---|
| 3,681,811 A | 8/1972 | Amelung et al. ............. | 15/165 |
| 3,718,978 A | 3/1973 | Van Koevering et al. .. | 33/174 L |
| 3,899,734 A | * 8/1975 | Beaver et al. ............... | 324/220 |
| 3,949,292 A | 4/1976 | Beaver et al. ................ | 324/37 |

(Continued)

FOREIGN PATENT DOCUMENTS

| | | | |
|---|---|---|---|
| DE | 196 24 275 A | 1/1997 | |
| DE | 200 02 929 U | 11/2000 | |
| FR | 2 667 519 A | 4/1992 | |
| WO | WO 98/12418 A | 3/1998 | |
| WO | WO 99/00621 | 1/1999 | |
| WO | WO 99/62042 | * 5/1999 | ........... G08C/19/00 |
| WO | WO 00/61988 | 10/2000 | |

OTHER PUBLICATIONS

U.S. Appl. No. 09/547,281, filed Apr. 12, 2000, Schempf et al.

Primary Examiner—Rita Leykin
(74) Attorney, Agent, or Firm—Kirkpatrick & Lockhart Nicholson Graham LLP

(57) ABSTRACT

The present invention provides a long-range, untethered, live, in-pipe inspection system that includes a self-propelled train having a plurality of modules; joint members for interconnecting adjacent modules, data collection components, and wireless communication components for transmitting collected data and receiving control messages. The module-train includes, generally, at least one, and preferably two drive modules, at least one power module and an electronics module. The train may additionally include at least one support module, which may be interposed between the power and electronics modules. In one embodiment of the invention, there are two drive modules, one at each terminal end of the train, two power modules, one adjacent to each drive module, two support modules, one adjacent to each power module, and one central electronics and computing module.

108 Claims, 22 Drawing Sheets

U.S. PATENT DOCUMENTS

| | | |
|---|---|---|
| 3,967,194 A | 6/1976 | Beaver et al. ................. 324/37 |
| 4,006,359 A | 2/1977 | Sullins et al. ............ 250/358 P |
| 4,252,152 A | 2/1981 | Martin et al. ................. 138/97 |
| 4,445,088 A | 4/1984 | Schubel ...................... 324/238 |
| 4,473,921 A | 10/1984 | Weber et al. ................. 15/304 |
| 4,563,841 A * | 1/1986 | Hart et al. ...................... 451/2 |
| 4,601,204 A * | 7/1986 | Fournot et al. ............ 73/866.5 |
| 4,648,454 A | 3/1987 | Yarnell ........................ 166/297 |
| 4,839,593 A | 6/1989 | Spies ........................... 324/240 |
| 4,843,319 A | 6/1989 | Lara ............................ 324/240 |
| 4,843,320 A | 6/1989 | Spies ........................... 324/240 |
| 4,852,391 A * | 8/1989 | Ruch et al. ............... 73/40.5 R |
| 4,862,808 A * | 9/1989 | Hedgcoxe et al. ........ 104/138.2 |
| 4,941,511 A | 7/1990 | Johansen et al. ............. 138/89 |
| 4,991,651 A * | 2/1991 | Campbell .................... 166/122 |
| 5,172,639 A | 12/1992 | Wiesman et al. ........ 104/138.2 |
| 5,203,741 A * | 4/1993 | Turner et al. ................ 464/111 |
| 5,363,935 A * | 11/1994 | Schempf et al. ............. 180/9.1 |
| 5,388,528 A | 2/1995 | Pelrine et al. ................. 105/78 |
| 5,416,944 A | 5/1995 | Eriksson ................... 15/104.09 |
| 5,461,313 A * | 10/1995 | Bohon et al. ............... 324/240 |
| 5,528,789 A | 6/1996 | Rostamo ................... 15/104.12 |
| 5,550,953 A * | 8/1996 | Seraji .......................... 700/263 |
| 5,704,838 A * | 1/1998 | Teale ............................ 464/19 |
| 5,736,821 A * | 4/1998 | Suyama ........................ 318/16 |
| 5,773,984 A | 6/1998 | Suyama ...................... 324/635 |
| 5,878,783 A * | 3/1999 | Smart ........................... 138/93 |
| 5,899,795 A | 5/1999 | Penza ........................... 451/61 |
| 6,031,294 A * | 2/2000 | Geis et al. ..................... 290/52 |
| 6,087,830 A * | 7/2000 | Brandly et al. ............. 324/220 |
| 6,107,795 A * | 8/2000 | Smart ........................ 324/220 |
| 6,123,027 A | 9/2000 | Suyama .................... 104/138.2 |
| 6,222,946 B1 * | 4/2001 | Abe ............................ 382/281 |
| 6,243,657 B1 * | 6/2001 | Tuck et al. .................. 702/150 |
| 6,260,501 B1 * | 7/2001 | Agnew ....................... 114/257 |
| 6,339,993 B1 * | 1/2002 | Comello et al. .......... 104/138.2 |
| 6,450,104 B1 * | 9/2002 | Grant et al. .............. 104/138.2 |
| 6,553,322 B1 * | 4/2003 | Ignagni ....................... 702/34 |

\* cited by examiner

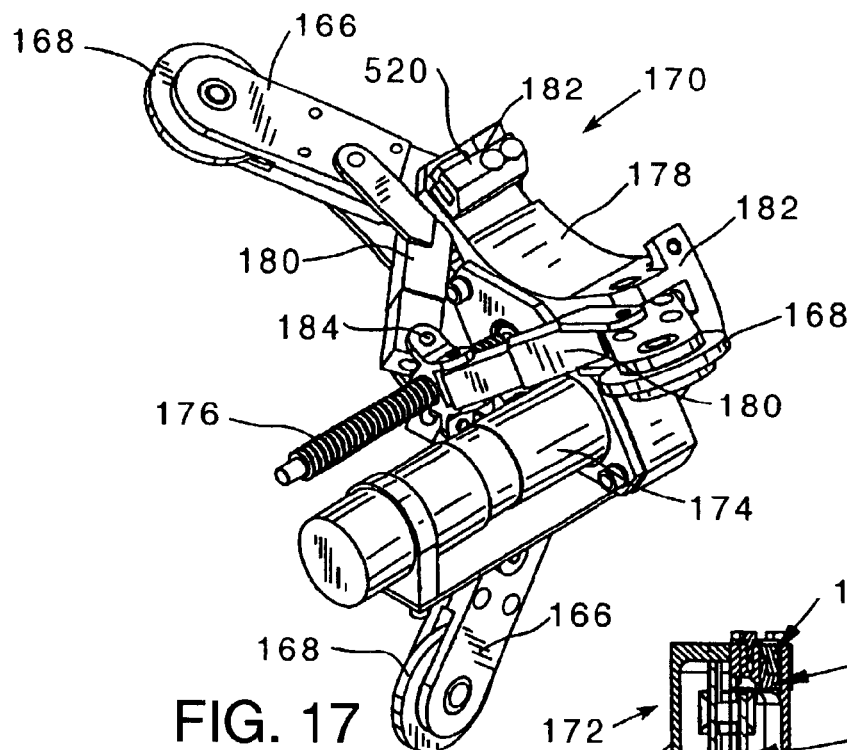
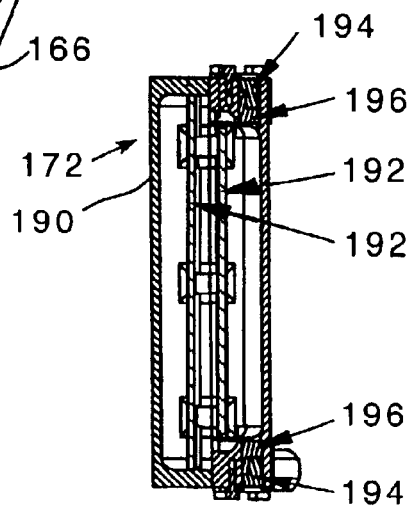
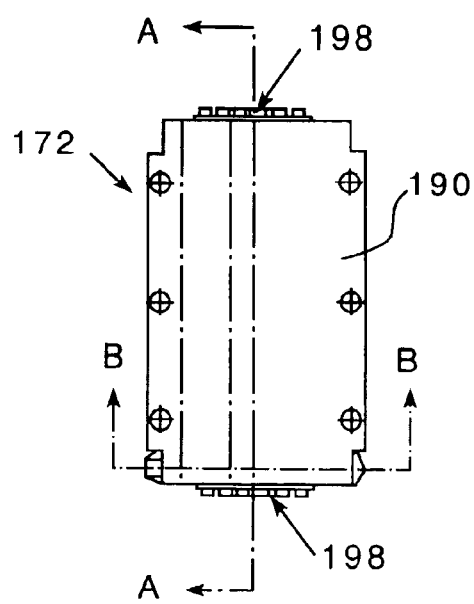
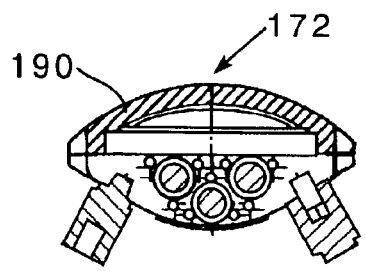
FIG. 17
FIG. 16B  SECTION A-A
FIG. 16A
FIG. 16C  SECTION B-B

SECTION A-A

GAS MAIN ROBOTIC INSPECTION SYSTEM

The present application claims priority from U.S. Provisional Patent Application Ser. No. 60/273,845 filed Mar. 7, 2001.

BACKGROUND OF THE INVENTION

The present invention relates to self-propelled robotic systems for inspecting pipelines, particularly, live gas pipelines.

Gas distribution utilities nationwide are coming under ever-increasing pressure to maintain, upgrade and efficiently operate their underground natural gas distribution and delivery system. To do so, these utilities use a vast array of technologies to monitor, inspect, repair, rehabilitate and replace their underground pipelines. More and more piping needs to be inspected due to the age of the existing urban gas-pipeline distribution network. Currently, little to no internal inspection is performed on a line that is known or assumed to be leaking in one or more locations, without at least one of them being sufficiently major to warrant immediate action. The operating company has to make a decision as to whether to spot- or section-repair the line, reline it or completely dig it up and replace it—these decisions are typically made based on in-situ evidentiary data (maps, historical repairs, leak surveys, corrosion data, etc.) to help the operator make a safe and cost-effective decision. Due to logistical and financial considerations, repairs and line replacement are only performed in the case of multiple-location or single-location leaking sections of pipeline. Most of the time though, the decision to replace and/or reline an existing gas line is not always supported by physical evidence that the line to be replaced actually needs to be replaced along its entire length, rather than just in certain stretches or maybe even only in certain spots.

The overall assessment and repair process can thus be extremely costly without the ability to judge the most cost-effective repair approach. In the US alone, over $650 million per year is spent to repair leaks of all types—giving the utilities the tools needed to make the decisions for cost-effective repair-method selection would have a drastic impact on their operations.

These pipe mains are ageing rapidly. One of the biggest tasks facing the industry is to perform in-situ inspection using a vast array of inspection sensors, so as to ascertain the state of the main prior to making decisions as to what maintenance steps to take. Information about the state of the network, both in terms of structure (pipe-integrity, corrosion, cracks, leaks, etc.), as well as process properties (pressure, flow, humidity, etc.) is desirable for maintaining pipe systems. Such data is typically only available after a local inspection survey is performed, either visually via a camera, or through other pipe-structure sensor systems (Magnetic Flux Leakage (MFL), UT, eddy-current, etc.). Based sometimes on this, but mostly on no concrete data at all, managers have to make a decision as to whether to repair, reline or replace (typically with plastic) their mains. Real-time data as to the internal state of a line would be immensely helpful to them to make a decision as to what course of action to take.

SUMMARY OF THE INVENTION

The present invention provides a long-range, untethered, live, in-pipe inspection system. The system includes a self-propelled train having a plurality of modules, joint members for interconnecting adjacent modules, data collection components, and communication components for transmitting collected data. The joint members are configured to allow articulation of the modules relative to each other through multiple planes and angles. The joint members may be universal type joints.

The plurality of modules may include two terminal modules, one positioned at each end of the train and a plurality of mid train modules positioned between the terminal modules. In this embodiment, the joint members of the system may comprise a double-axis steerable interconnect joint positioned between each terminal module and the mid-train module adjacent thereto, wherein the double-axis interconnect joint being movable about two axes of rotation and a single-axis steerable interconnect joint positioned between adjacent mid-train modules, wherein the single-axis interconnect joint being movable about a single axis or rotation.

The communications components may transmit collected data among the various modules and/or may transmit data to a remote receiver using wireless, fiber optics or other suitable communications methods. The communications components may also receive from a remote location.

Each module of the train has a central axis and at least one of the joint members may be configured for rotation about a first axis generally perpendicular to the central axis of the module to which the joint member is interconnected and may further be configured for rotation about a second axis generally parallel to the central line of the module to which the joint member is interconnected.

In one embodiment of the invention, the plurality of joint members may include at least one double-axis steerable interconnect joint comprised of a first interconnect unit positioned on one of the modules and rotatably and pivotally connected to a second interconnect unit positioned on an adjacent one of the modules. The plurality of joint members may further include a single-axis steerable interconnect joint comprised of a third interconnect unit positioned on one of the modules and rotatably connected to a fourth interconnect unit positioned on an adjacent one of the modules, wherein the modules interconnected by the single-axis interconnect joint having no more than one module in common with the modules interconnected by the double-axis interconnect joint.

The first interconnect unit of the embodiment just described may comprise a first mounting member positioned on an end of a module in facing relationship to an end of an adjacent module, a first steering motor assembly, and a first gear assembly operatively connected to the first steering motor assembly, wherein a portion of the first gear assembly is positioned for rotation about a first axis of rotation. The first mounting member may include a pair of clevis mounts defining a space therebetween wherein the portion of the first gear is positioned in the space between the pair of clevis mounts. Alternatively, the first mounting member may comprises a swivel block rotatable about an axis of rotation parallel to the central axis of the module on which the swivel block is positioned, wherein the first axis of rotation is offset about ninety degrees relative to the axis of rotation of said swivel block.

The second interconnect unit of the embodiment just described may comprise a second mounting member positioned on an end of a module in facing relationship to an end of an adjacent module, a second steering motor assembly, and a second gear assembly operatively connected to the second steering motor assembly, wherein the portion of the second gear assembly is positioned for rotation about a second axis of rotation. The second mounting member may be in the form of the pair of clevis mounts described above wherein the portion of the second gear is positioned in the space between the pair of clevis mounts, or may be in the form of the swivel block described above, wherein the second axis of rotation is offset about ninety degrees relative to the axis of rotation of said swivel block.

Each of the third and fourth interconnect units of the embodiment of the joint members just described may comprise a single-axis mounting member positioned on an end of a module in facing relationship to an end of an adjacent module, a third motor assembly, and a third gear assembly operatively connected to the third motor assembly, wherein a portion of the third gear assembly is positioned for rotation about an axis of rotation. Each of the said single axis mounting members are preferably fixedly attached to their respective modules. The axis of rotation of the gear portion of the third interconnect unit is preferably substantially parallel to the central axis of the module on which the third interconnect unit is positioned, and the axis of rotation of the gear portion of the fourth interconnect unit is preferably offset from the central axis of the module on which the fourth interconnect unit is positioned by about ninety degrees.

The train includes, generally, at least one drive module, at least one power module and an electronics module. The train may additionally include at least one support module, which may be interposed between the power and electronics modules. In one embodiment of the invention, there are two drive modules, one at each terminal end of the train, two power modules, one adjacent to each drive module, two support modules, one adjacent to each power module, and one central electronics module. Other modules for performing specific tasks may be added to the module train.

The data collection components and data transmission components may be housed in the drive module.

The data collection components preferably include an imaging system. The imaging system may include a camera and a plurality of light sources, or may include any other suitable known image gathering systems, including systems for night vision wherein lighting is not necessary. However, the data collection components may additionally or alternatively include one or more of sensors for detecting magnetic flux leakage, sensors for detecting eddy currents, wheel follower odometers, accelerometers or potentiometers.

Data transmission is preferably in real time, and may be by means of an Ethernet link, radio wave, fiberoptics, electromagnetic currents or the like.

As used herein, "real time" means transmission of data substantially as it is collected without intermediate storage and artificial delays. Delays, if any, would be the expected difference in the time data is collected and the time necessary to wirelessly transmit the data as it is collected, or in some cases, following conversion to a usable format by computer analysis at the time of collection.

The drive mechanism is preferably housed in the drive module and may include a motor assembly, a drive shaft operatively connected to and driven by the motor assembly, a plurality of drive arms, each drive arm having at least one driven wheel rotatably attached at a free end of the drive arm and a gear assembly for translating movement of the drive shaft to the driven wheels to effect locomotion of the module-train. The drive mechanism may further include an extension shaft operatively connected to and driven by the motor assembly, a linkage assembly operatively connected to the extension shaft and to each of the plurality of drive arms for extending and collapsing the drive arms out of and into, respectively, the drive module.

The linkage assembly may include a plurality of extension arms, wherein each extension arm is pivotally connected to a different one of the drive arms, and an extension unit pivotally connected to each of the extension arms and operatively connected to the extension shaft for translating movement of the extension shaft to the extension arms.

The motor assembly may include a drive motor for driving the drive shaft and an extension motor for driving the extension shaft.

The power module of the module train may include a power source and means for transferring power from the power source to each of the drive mechanism, data collection components and wireless communication components. The power source is preferably a chemical energy source, such as a battery pack.

As discussed previously, the drive modules may include an imaging system. The imaging system may be a digital imaging system, and the drive modules may each include a low voltage differential signaling (LVDS) transmitter coupled to the digital imaging system thereof for serializing image pixel data captured by the imaging system. The LVDS transmitters may transmit the serialized image pixel data to a LVDS receiver in a central electronics module of the train. One of the signals from the two imaging systems may be selected for processing in the central electronics module by a multiplexer. The LVDS receiver may deserialize the received image pixel data so that the clock and pixel data may be extracted to rebuild a parallel image. The image data may be packetized and transmitted via a wireless network to a remote user-interface for review of the image by an operator.

BRIEF DESCRIPTION OF THE SEVERAL VIEWS OF THE DRAWINGS

The present invention will be better understood by reference to the attached drawings. Therefore, for purposes of illustrating the various embodiments of the inspection robot of the present invention and not for limiting the same, reference is made to the drawings, as follows:

FIGS. 16A–C illustrate an embodiment of the electronics unit of the support module of FIG. 11 wherein FIG. 16B is a side section view taken through the line A—A of FIG. 16A and FIG. 16C is an end section view taken through the line B—B of FIG. 16A.

FIG. 17 illustrates a perspective view of the idler arm mechanism of the support module of FIG. 13.

DETAILED DESCRIPTION OF THE PREFERRED EMBODIMENTS

Figure 1:
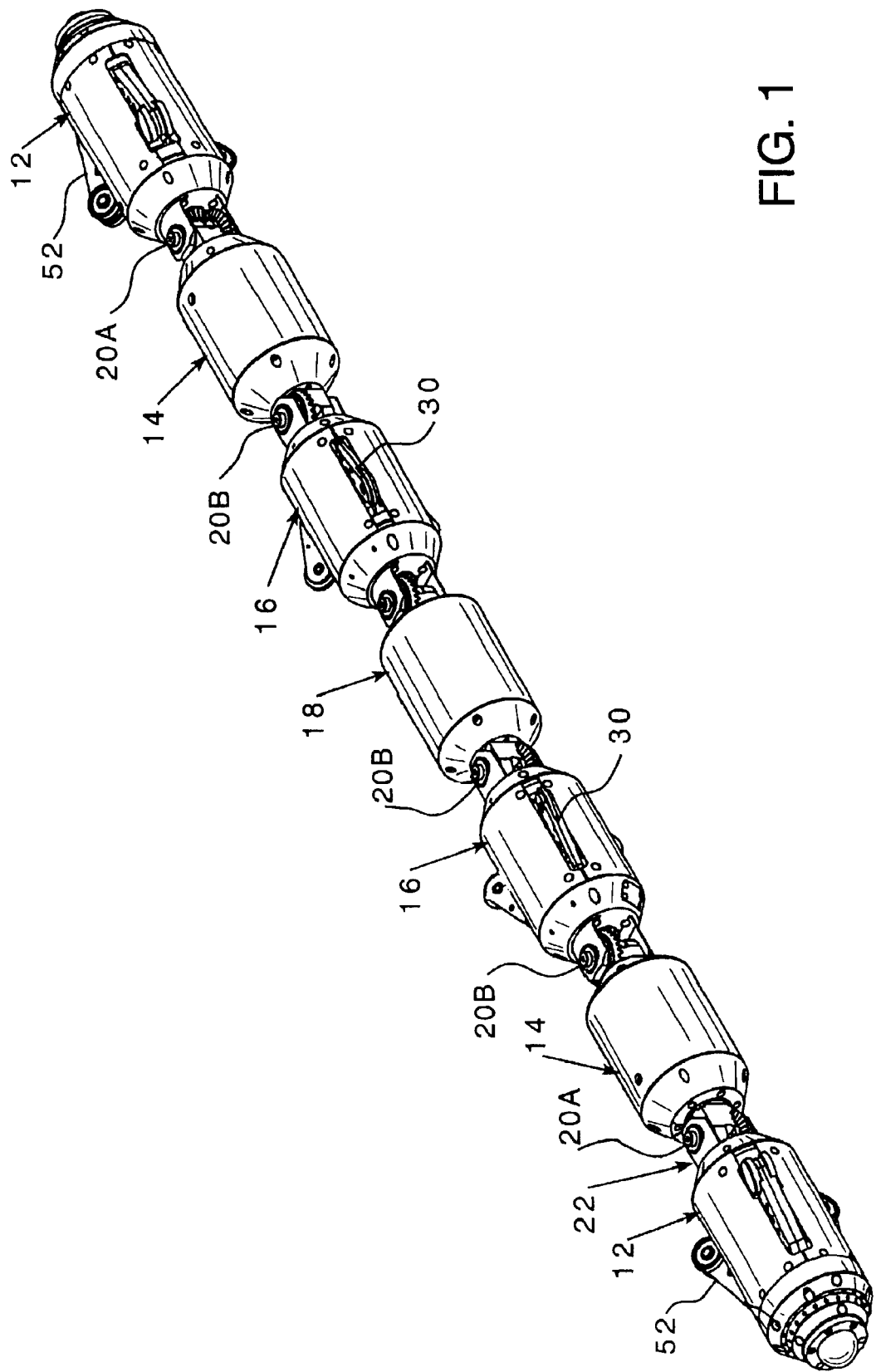
FIG. 1 illustrates an embodiment of the modular inspection robot of the present invention.

FIGS. 1 to 27 illustrate features of one or more possible embodiment of the inspection system 10 of the present invention. Referring to FIG. 1, the pipe inspection system 10 includes generally, a self-propelled train having a series of un-tethered modules, data collection capabilities and components for communication, such as wireless or cabled communication of the collected data, both among the various modules and to an operator or receiver in a remote location. The embodiment of the pipe inspection system 10 shown in FIG. 1 may include two drive modules 12, one positioned at each terminal end of the train, and at least one mid-train module. The mid-train modules shown in the drawings include two power modules 14 positioned inward of and adjacent to the drive modules 12, two support modules 16 positioned inward of and adjacent to the power modules, and a central electronics module 18, including computing capabilities. The modules 12, 14, 16 and 18 are joined to the adjacent module or modules by motorized movable joints members 20 comprised of first and second interconnect joints 20A and 20B. The first interconnect joints are steerable double-axis joints that can pitch and roll about the central axis of the module train, and which are positioned on the interconnect (inside) end of each drive module 12 and on the end of the power modules 14 adjacent to each drive module 12. The second interconnect joints are single-axis, pitch only joints positioned on one end each of the power modules 14, and on each end of the support modules 16 and the electronics module 18. The "pitch axis" or "pitch" as used herein means the axis perpendicular to the module train centerline when the train is resting on an even, linear surface. The "roll axis" or "roll" as used herein means the axis parallel to the centerline of the module train when the train is resting on an even, linear surface. These steerable interconnect joints allow the system to go forwards/backwards, into and out of turns, bends and Ts, etc. at substantially any angle through substantially any plane, limited only by physical impedance from the adjacent modules. Each drive module 12 includes a self-propelled drive mechanism 50 with drive arms 52 and traction wheels 28. The drive arms are spring loaded to allow the traction wheels to roll over small obstructions within the pipe, such as dirt or weldments. Passive spring-loaded wheel-follower arms 30 included in the support modules 16 center the remaining modules in the pipe.

In one embodiment of the invention, each axis of freedom is absolutely encoded with potentiometers. In the case of arm deployment, in addition to the potentiometer encoding, current to torque measurement is used to determine the normal force on the pipe wall in addition to absolute arm angle determined by the potentiometer. Pitch and roll axes are encoded with absolute angle position and are driven in a closed loop to a desired angle by a stepper motor through a set of gears.

The two drive modules 12 on either end of the train-like system 10 contain the drive-section with the expandable centering legs and internal wheel drive-train, as well as the data collection components, such as video-imaging and lighting systems. The power and lighting components, as well as the video-signal amplification components, are preferably integrated into module 12, which may include a frontal protection-ring to avoid scarring the lens during deployment and operations.

The central electronics module 18 contains the computer system, while the two inboard power modules 14 contain the preferably rechargeable battery-cells with monitoring, safety- and state of charge electronics.

Data collection may be by means of sensors, including but not limited to, wheel-follower odometers (encoders), front & rear tri-axial accelerometers, and end-mounted cameras with dedicated lighting. In low pressure mains having iron pipes, for example, a camera can be used to view water leakage corrosion and breaks. In high pressure mains having, for example, steel pipes, there is typically little corrosion to see, so data collection may be by other means, such as eddy current, magnetic flux leakage and other non-visual means of data collection. Communications may be provided through the medium in the pipe, use of the pipe walls as wave guides or otherwise with fiber-optics in a tethered connection, using radio waves, acoustics, and/or low frequency electro-magnetics. For example, communications may be over a 2.4 GHz wireless Ethernet link to an off-board control-panel computer in a rugged enclosure. The system 10 is rendered safe for operation in the natural gas environment by way of evacuation, purging and two-way check-valving of each module to reduce weight and avoid entrapment of oxygenated gases. Thus, there is no need for pressure-sealed enclosures. For added safety, however, the power modules 14 may provide a pressurized environment if the cells cannot withstand differential pressures.

Each of the foregoing features will be described in more detail herein.

The drive module 12 is shown in more detail in FIGS. 2 through 5. The drive module 12 includes generally, a housing 40, a front end cap 42, a rear interconnect cap 44, a drive mechanism 50, and an electronic stack 60 comprising data collection components and data transmission components. The front end cap 42 has an optical dome 46, a dome retainer 48 with associated fasteners (not shown) to attach the dome retainer 48 to the front end 42 and charging contacts 47 for use in recharging the battery packs of power modules 14. A plurality of lighting elements 24, such as white LED components, and the electronics stack 60 are positioned within front end cap 42. The lighting elements 24 should be sufficient in number and/or intensity, to provide light for viewing the interior of a pipeline.

Figure 10:
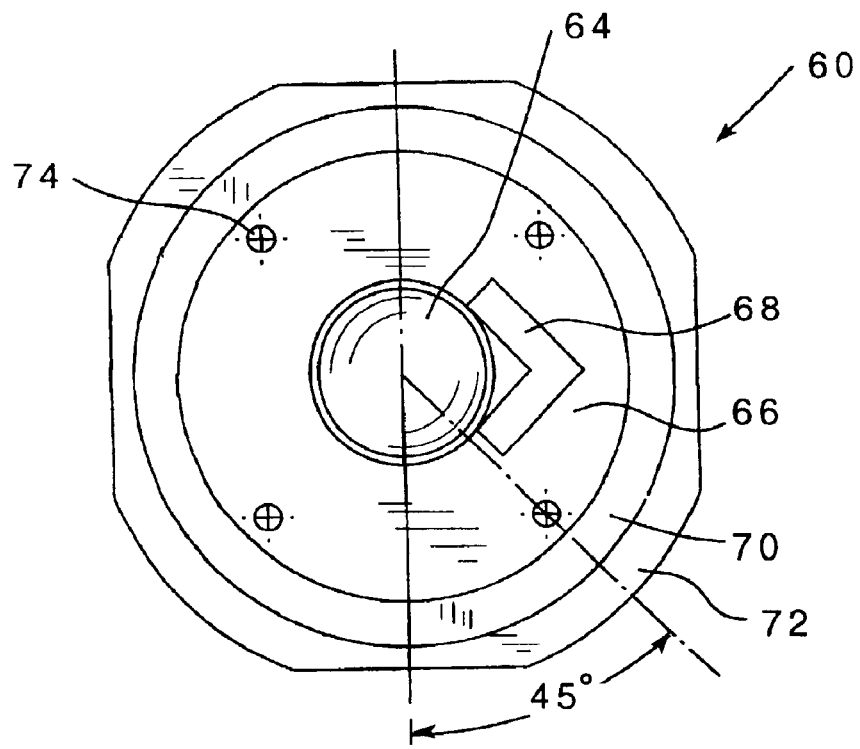
FIG. 10 illustrates the top plan view of an electronics stack, including an inverted F antenna used in one embodiment of the inspection robot of FIG. 1.
Figure 11:
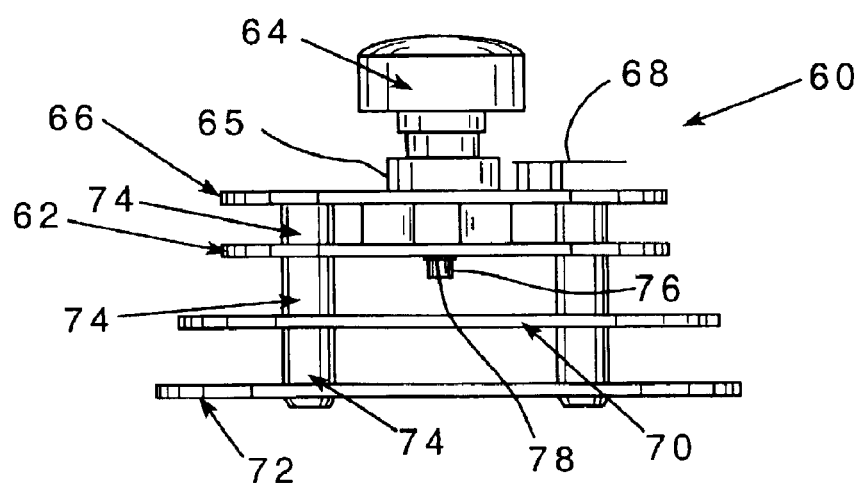
FIG. 11 illustrates a side view of the electronics stack of FIG. 10.

Referring to FIGS. 10 and 11, the electronics stack 60 includes a camera circuit board 62, a lens 64, and lens mount 65 for collection of visual data, an antenna reflector board 66 with an inverted F antenna 68 for data communication, and two drive module circuit boards 70, 72 for control of the drive mechanism 50. The boards are separated by spacers 74. A fastener 76, such as a set-screw, pin or the like, and washer 78 attach the lens 64, lens mount 65 and camera and antenna reflector boards 62, 66.

Fasteners 82 secure the electronics stack 60 to front end cap 42. End caps 42, 44 may be sealed to housing 40 by seal screws 84 and O-rings 86. (See FIG. 3) A feed conduit 88 provides a path for electrical connections from the electronic stack 60 to drive mechanism 50.

Several options for implementing the forward/rearward looking color camera systems are described. They differ only in the choice of optics and software, but have a drastic impact on capability and packaging. The first is based on a standard 60-degree to 90-degree FOV lens mounted to a single-board camera, with a CCD or CMOS imager with at least TV-resolution (640H×480V), implying an image-resolution of almost 310,000 pixels.

When lighting is needed in the imaging system, due to the compactness of the lens used in the environment of a pieline, clusters of light emitting diodes (LEDs) can be arranged in circular fashion around the lens, yet physically-separated from the lens to avoid internal reflections, and frame phase-synched to the camera frame rate to maximize luminosity without wasting power. The lighting system may therefore, consist of a set of 40 high-intensity white LEDs 24, arranged in a circular fashion around the lens. Half the LEDs are forward looking and half are directed radially, at an angle to the pipe-wall, to allow the system to see a half-sphere.

The purpose of the camera is to map the walls of gas pipes. For geometric reasons (i.e., to get the best picture with the most information) the part of the wall directly outside of the module's front is of particular interest. Any camera that will fit into the available space of the pipe line may be mounted for use on the drive module 12. However, the single board camera using low voltage differential signaling camera interface is preferred. To obtain a good view of the band surrounding the head of the module, a wide-angle lens, in the range of 120 degree to 150°, or a 180° "fisheye" lens may be used.

A ⅓" CMOS imager with 640×480 layer encoded pixels, or a CCD color camera device may be used. The image is displayed by any suitable known, or hereafter developed, means, such as the video channel of any TV or PC monitor, such as the display shown in FIG. 25. The means of transmitting the visual images from the camera in the drive module 12 to the processor in the electronics module 18 will be described in more detail herein in connection with the computer architecture of the system 10.

The system 10 may utilize NASA's mosaiquing software and provide exceptional imagery of sidewalls and features without the need for any moving parts (as in a pan/tilt camera). This is believed to be the most efficient way of storing live image data. Other software may be written by a programmer to achieve the same effect.

The continuous video footage of pipe condition within miles of piping of any distribution network, provides the necessary information to the maintenance division of any utility to permit them to decide upon the location, repair-method and scheduling of repairs, if any. The system 10 is able to detect (i) water infiltration, (ii) accumulated debris, and (iii) abandoned and live service connections. It can (i) locate main reducing fittings and offsets, (ii) verify location (counting joints and reset-measuring and adding pipe-lengths) and path of main (by use of a sonde), and (iii) provide a visual evaluation of internal pipe conditions.

The availability of such a long-range and easily deployable tool will greatly enhance the diagnostic and maintenance budgeting for existing gas operators, with the potential to save large cost in terms of providing the data to make decisions as to which repair/replacement method (spot/local/complete-line replacement/relining) to utilize. In addition, such a system may also be used as an emergency maintenance tool, by assisting in locating (i) water infiltration into a low pressure gas mains, (ii) cracked cast-iron gas mains and damaged steel mains, and (iii) water pools and obstructions due to the presence of foreign material in the pipe.

Figure 3:
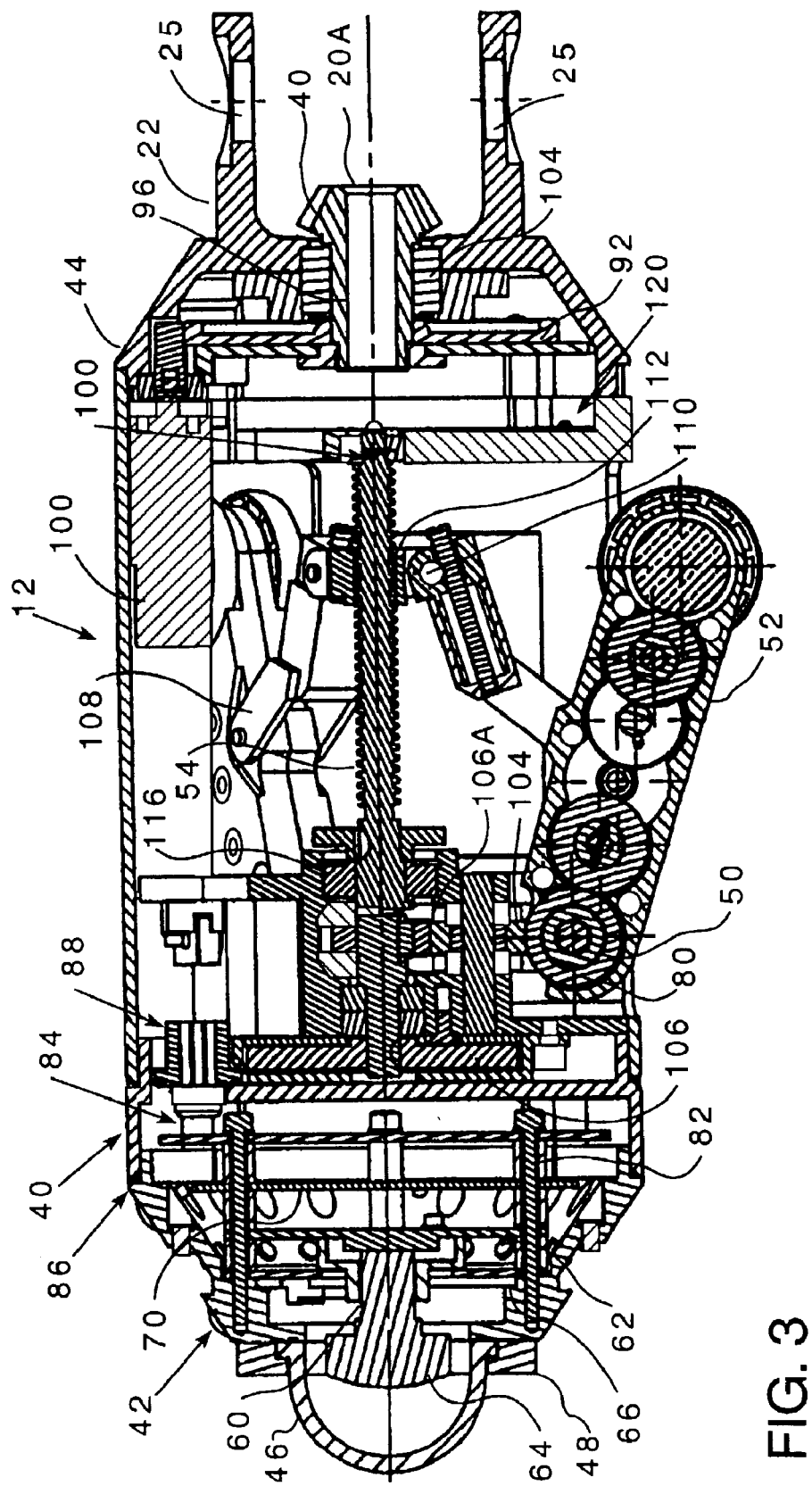
FIG. 3 illustrates a side section view of the drive module of FIG. 2.
Figure 4:
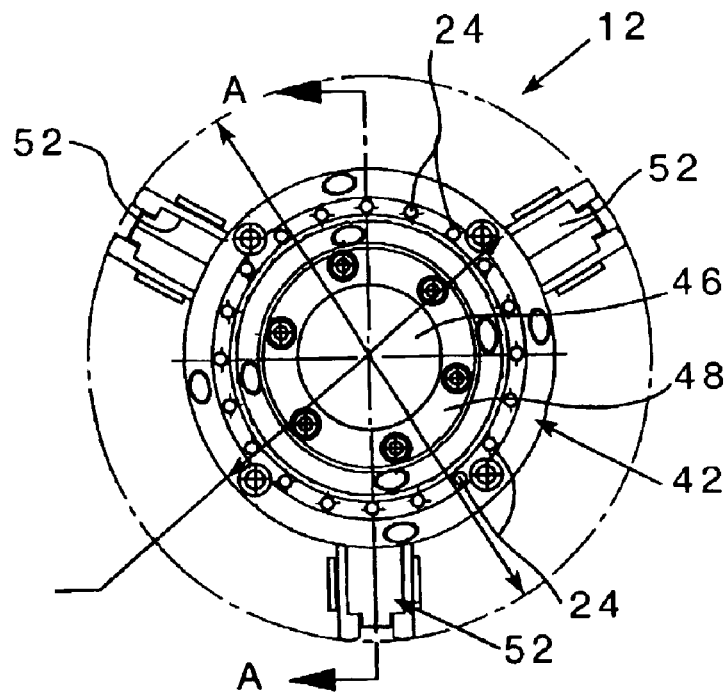
FIG. 4 illustrates a front-end view of the drive module of FIG. 2.
Figure 5:
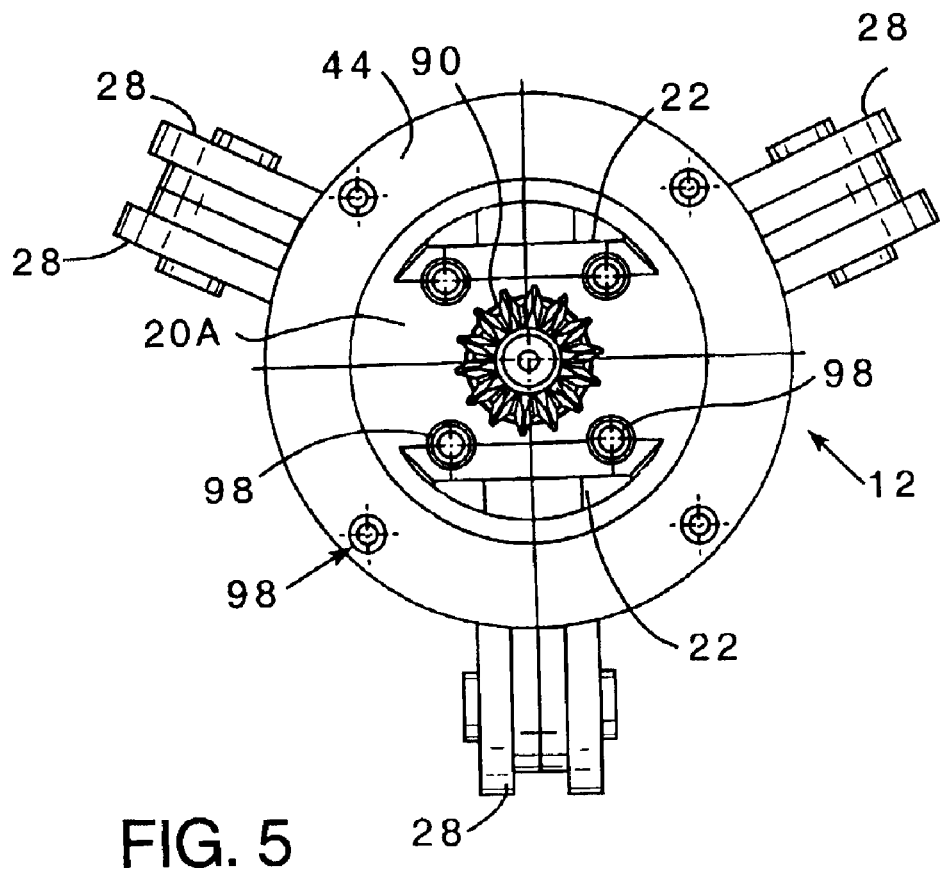
FIG. 5 illustrates a rear view of the drive module of FIG. 2.
Figure 6:
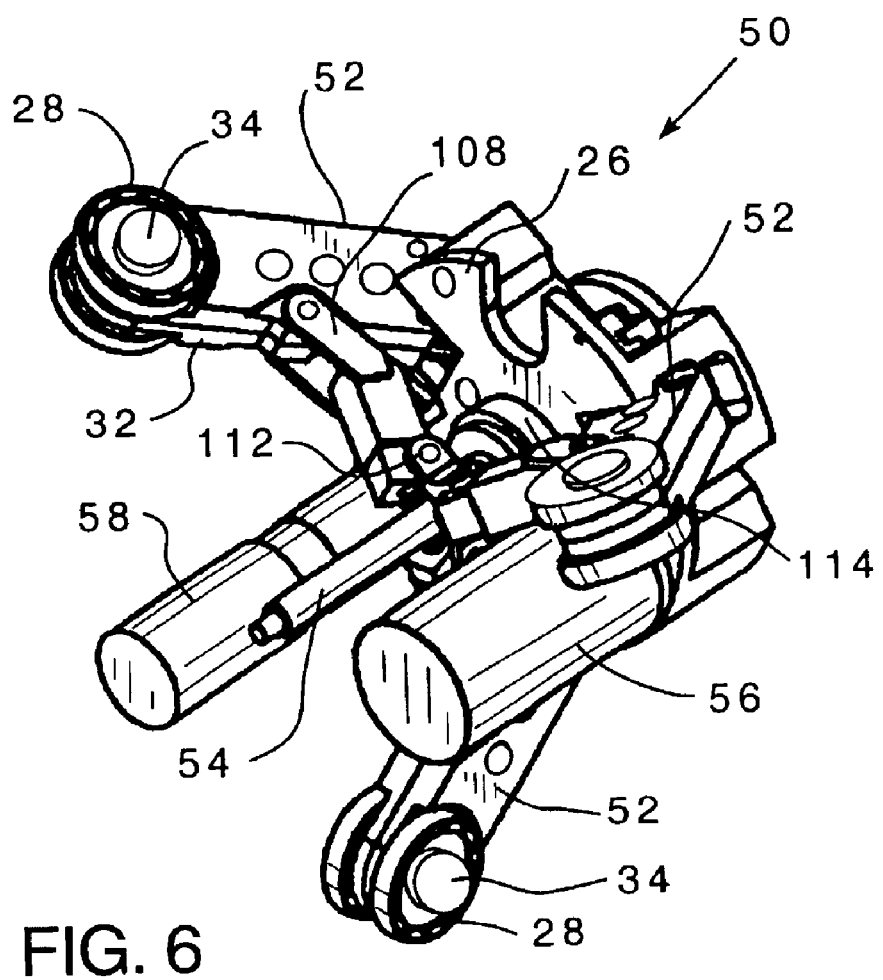
FIG. 6 illustrates a perspective view of the drive mechanism of the drive module of FIG. 2.
Figure 7:
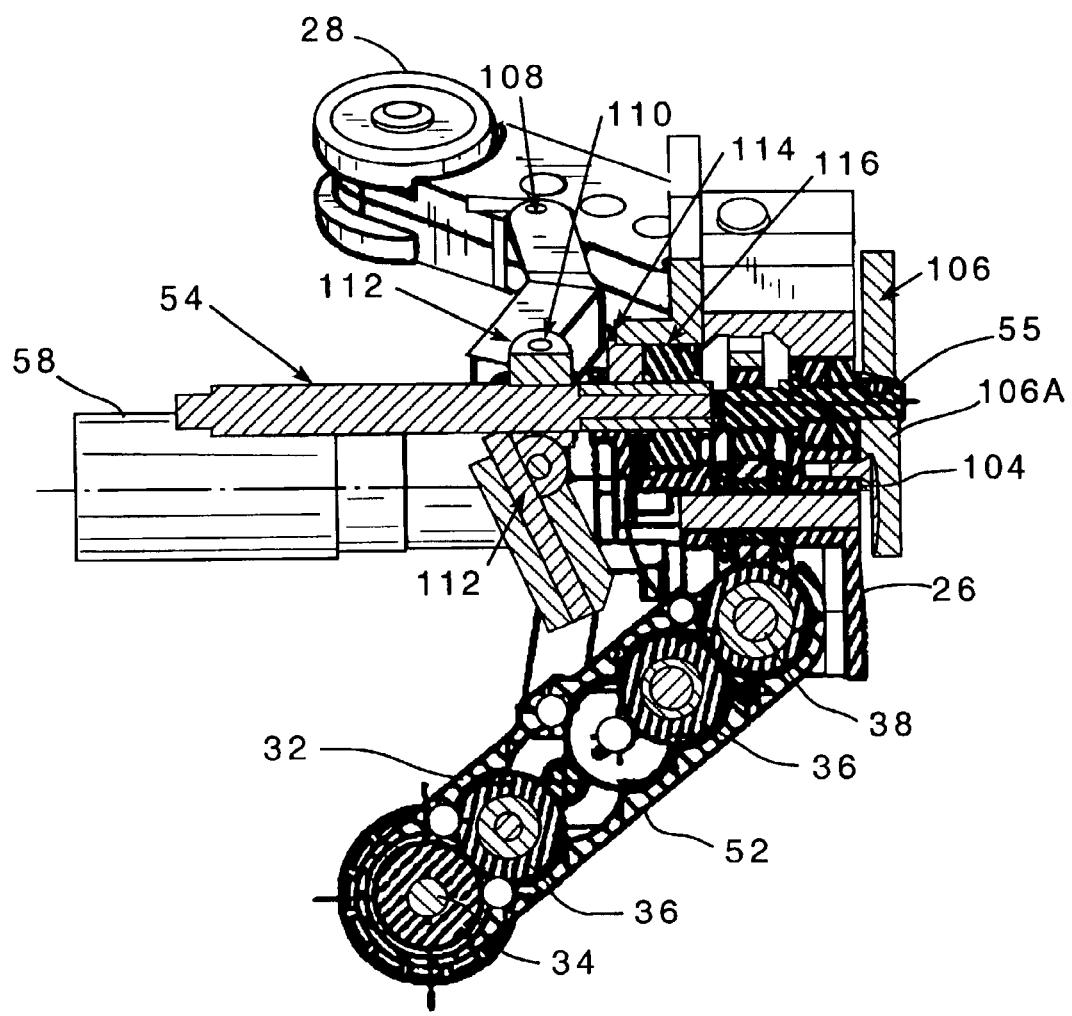
FIG. 7 illustrates a section view of the drive mechanism of FIG. 6.
Figure 8:
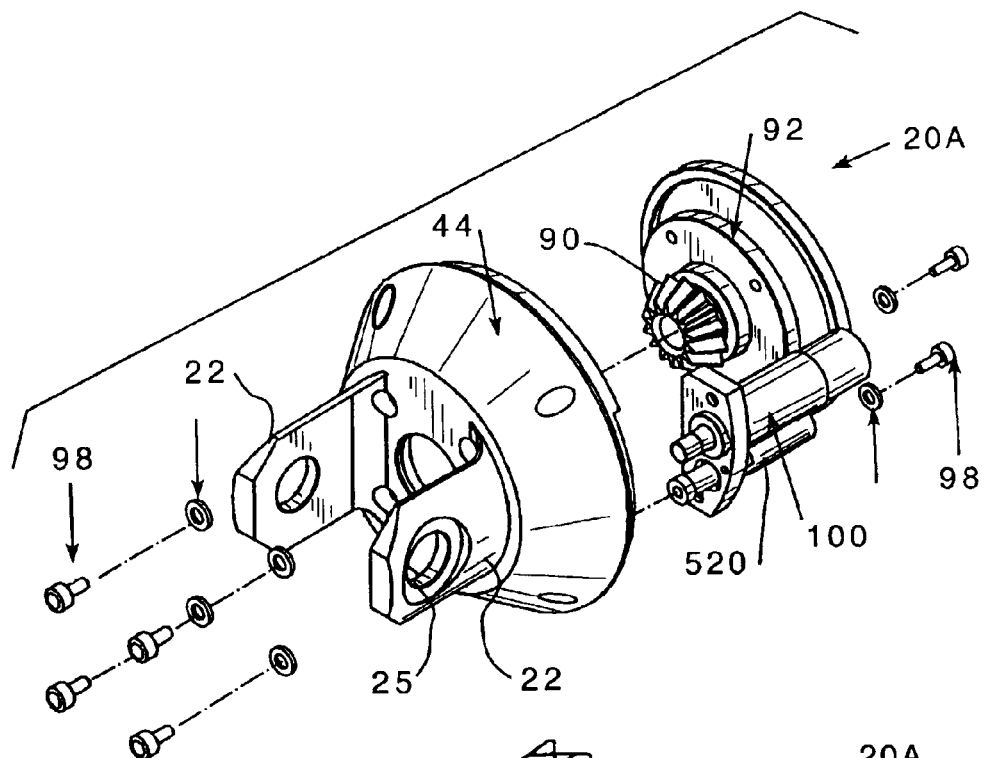
FIG. 8 illustrates an exploded view of the components of the two-axis interconnection joint of the drive module of FIG. 2.

The embodiment of drive mechanism 50 shown in FIGS. 3, 6 and 7, includes, generally, a base 26, three drive arms 52, three extension arms 108, a drive shaft 55, a lead screw 54, a drive motor 56 and a lead screw motor 58. Lead screw 54 is supported at one end by base 26 and at the other end by the center of a lug ring 120. Drive motor 56 drives drive shaft 55 through drive gear 106. The drive shaft 55 drives gear 106A, which may be a helical-type gear with a 45° helix angle. Gear 106A drives gear 104, which may also be a helical type gear with a 45° helix angle, but of opposite "hand" (helix angle) to gear 106A. The axis of gear 104 is parallel to the axis of gear 106A. Gear 104 drives gear 80, which may also be a helical type gear with a 45° angle of the same "hand" as gear 104. The axis of gear 80 is perpendicular to the axis of gear 104 and is coincident with the pivot axis of drive arm 52.

Lead screw motor 58 drives lead screw 54. Each drive arm 52 includes a drive arm housing 32 and, at its free end, two driven traction wheels 28 and an output gear 34 connecting the two wheels. The drive arm housing contains a series of successively meshed gears 36 to transmit the rotation from gear 80 to the drive wheels 28. A pivot pin 38 pivotally connects the drive arm 52 to the base 26. The drive shaft 55 is connected to a main drive gear assembly 106, which includes sub-gear 106A, the rotation of which is translated to a helical gear idler assembly 104, which in turn effects the movement of the drive chain gears 36, which is translated to drive wheels 28. A gear 114 is positioned around, and is driven by, lead screw 54. A bearing member 116 is positioned between lead screw 54 and the sides of base 26.

The locomotion system for system 10 is contained in its entirety in identical modules at the front and rear of the module-train. The locomotion mode provided by drive mechanism 50, due primarily to its power-efficiency and combined progress travel-speed, combines a powered wheel-driven pre-loadable and adjustable hybrid-locomotor into a single unit. The architecture of the module 12 is such that the drive-mechanism 50 has the ability to collapse its articulated driven arms 52, allowing it to ride on the bottom of a pipe, but expand to self-center itself in pipe, for example, a 6- and 8-inch inner diameter pipe. As shown in the figures, the arms are articulated by a linkage assembly and are powered by a single motor. The motor drives a spur-gear pass, powering the lead screw, to which a common extension unit 112 is attached, which drives the linkage assembly so as to extend or collapse the arms 52. An anti-rotation configuration keeps the extension unit from rotating, thereby causing only linear travel. As shown, the wheels 28 at the end of each arm 52 are all synchronously driven by a single motor through a planetary gear-reduction, with a pass-thru gear-train inside each arm, which then powers the dual set of wheels 28 at each arm. The wheel achieves traction due to the compression of the wheel against the inside pipe-wall.

Figure 2:
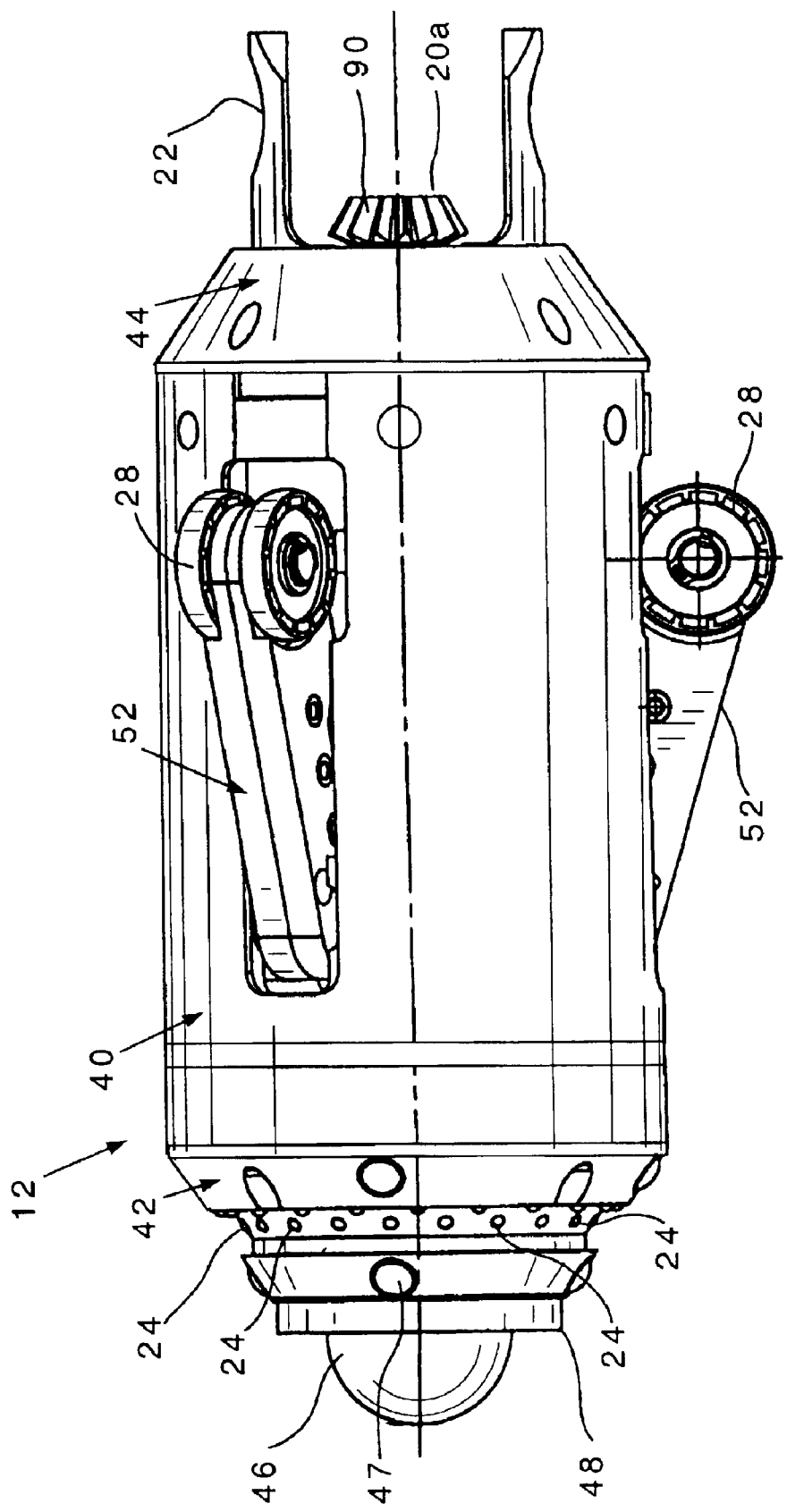
FIG. 2 illustrates an embodiment of the drive module of the inspection robot of FIG. 1.

Referring to FIG. 7, at about the middle of each drive arm 52, the arm 52 is pivotally connected to a first end of one of the two-part extension arms 108. Each extension arm 108 includes an internal spring and a series of spring washers around a center pin (See FIG. 3). Each arm 108 is pivotally connected at a second end by a pivot pin 110 to a common extension unit 112. The common extension unit 112 defines an annulus through which the lead screw 54 passes. Rotational movement of lead screw 54 carries extension unit 112 along the length of lead screw 54, thereby effecting the pivotal movement of extension arm 108 about pin 110 and the expansion and collapse of drive arms 52, either outwardly or inwardly relative to the housing 40. The housing 40, as shown in FIG. 2, has three openings along its sides to receive each of the three drive arms 52. Each drive arm 52, two-part extension arm 108 and extension unit 112 define a linkage-slider combination to effect movement of the drive arms 52.

The steering capability for system 10 may be provided by actuation in two degrees of freedom of the double-axis interconnect joint 20 situated between each drive module 12 and power module 14. One end cap houses a motor and gear assembly, which may be in the form of a stepper motor-gearbox combination, mounted off-axis, driving a bevel-gear through a shaft-mounted pinion. The central shaft mounted to the bevel-gear has a hollow-shaft that penetrates the end cap, allowing wires to be routed through it, and hooks up with a bevel pinion-gear. The pinion gear then engages a sector bevel-gear that is coaxial with the u-jointed bearing-supported shaft around which the axis rotates.

Figure 9:
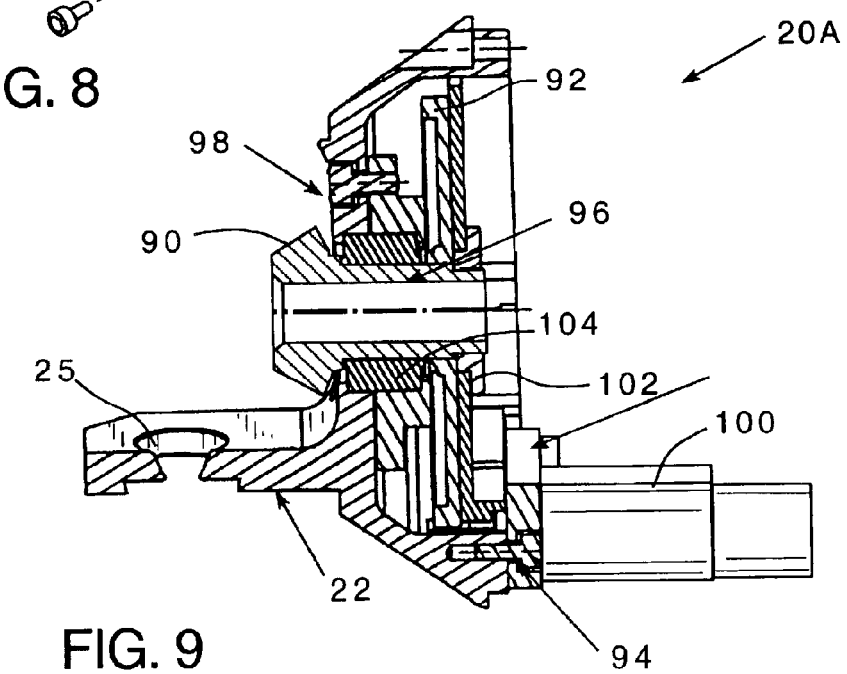
FIG. 9 illustrates a section view of the assembled two-axis interconnection joint of FIG. 8.

Rear interconnect cap 44 includes a double-axis joint, having a first interconnect unit 20A, comprised of opposing devises 22 and an opening through which the beveled gear sector of bevel gear pinion 90 protrudes. Clevises 22 have openings 25 for receiving a pin to couple the first interconnect unit to a second interconnect unit of the double-axis joint on the adjacent end of power module 14. These interconnect units can be moved about the pitch axis (perpendicular to the center line of the module train) and the roll axis (parallel to the center line of the module train). The motor 100 for the pitch axis is shown in the figures as being in the drive module 12 and the motor for the roll axis is shown in the figures as being in the power module 14. Other arrangements may be employed. Pinion-bevel gear 90 has beveled gear teeth on the contact end and a shaft 96 and is mounted for rotation on gear plate and active interconnect stage 92 by retainer nut 102. A bearing is provided around shaft 96 of gear 90. Interconnect motor 100, a stepper motor-gearbox combination, is attached, off-set from the center line of the module 12, to rear interconnect cap 44 by any suitable fastener, such as a screw or pin 94. As shown in FIGS. 3 and 9, interconnect motor 100 is operatively connected to gear 90 through gear plate and interconnect stage 92, driving the bevel-gear pinion 90 through a reduction gear set. The bevel gear pinion shaft 96 drives the bevel gear sector 90, which is mounted to a swivel block. The axis of the bevel gear sector 90 is coincident with the axis of the opposing devises 22 on the drive module end cap 44 to effect a range of motion of about 160°, plus or minus 80°, in a clockwise or counterclockwise direction about the axis of shaft 96. Any suitable fasteners 98 may be used to secure the components of the rear interconnect cap 44 together.

Figure 12B:
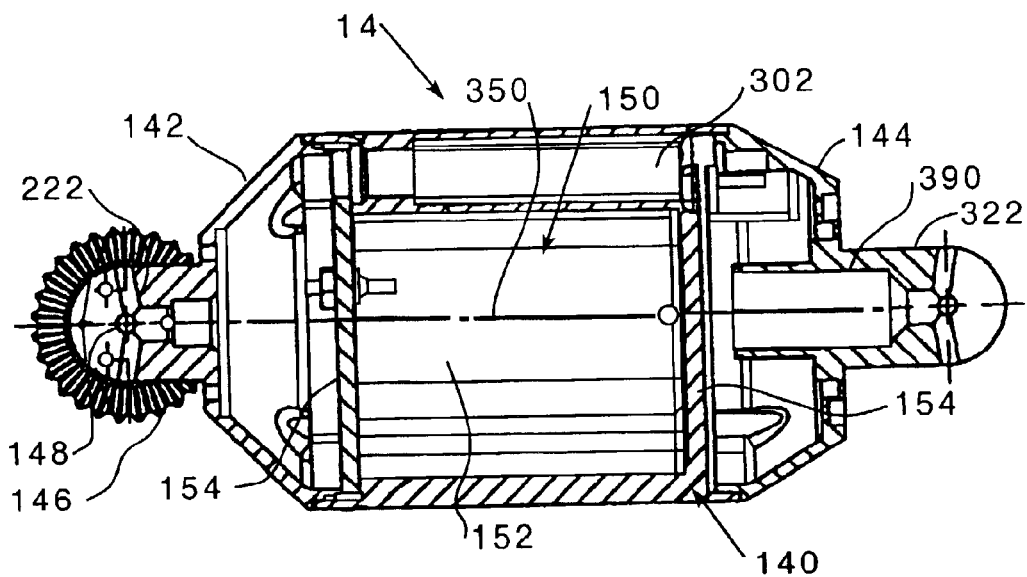
FIGS. 12(A) and (B) illustrate a perspective view and a section view, respectively, of an embodiment of the power module of FIG. 1, showing the two axis and single axis interconnection units at respective ends thereof.
FIGS. 12(C)–(F) illustrate views of the two axis interconnect unit of the power module as follows: a perspective view (C), an end view (D), a section view through the lines A—A of FIG. 12(D) (E) and a section view through the lines B—B of FIG. 12(D) (F).
Figure 12A:
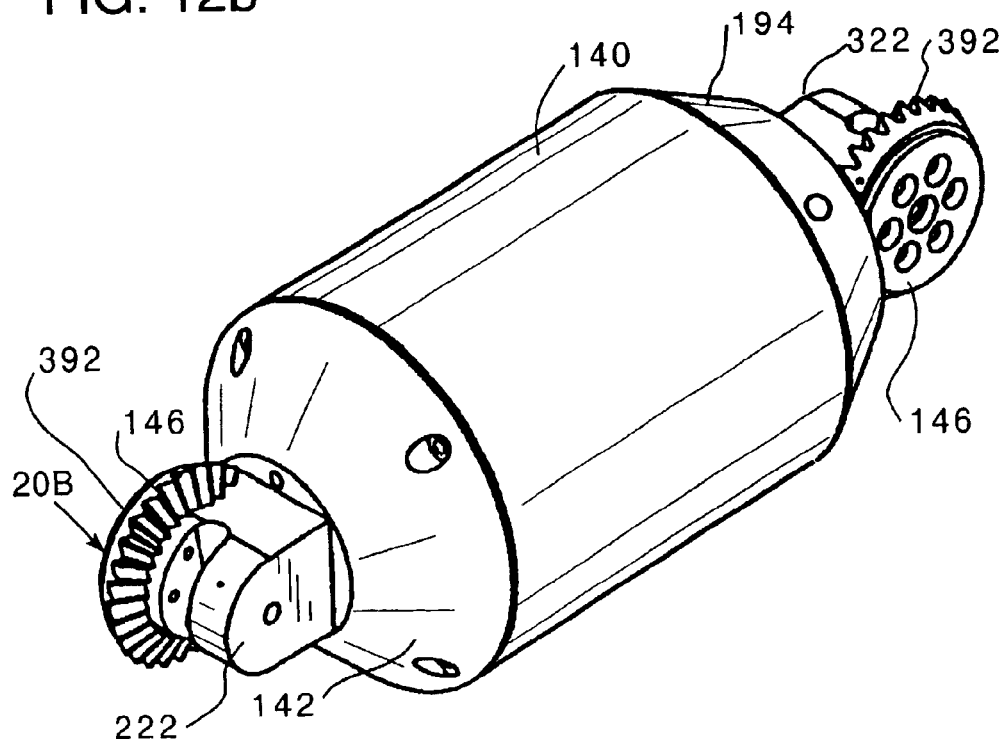
Figure 12C:
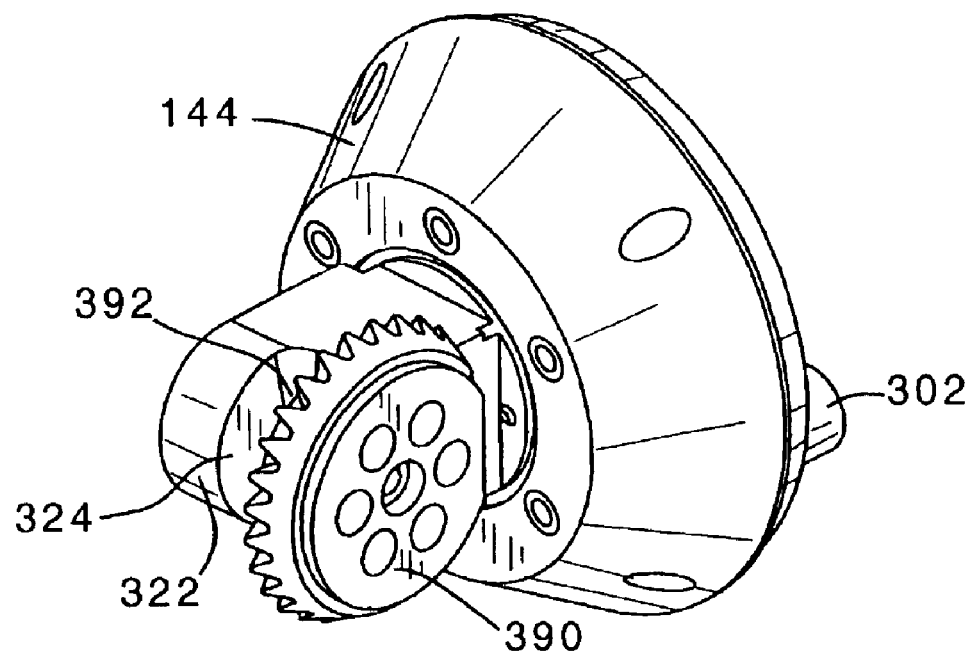
Figure 12D:
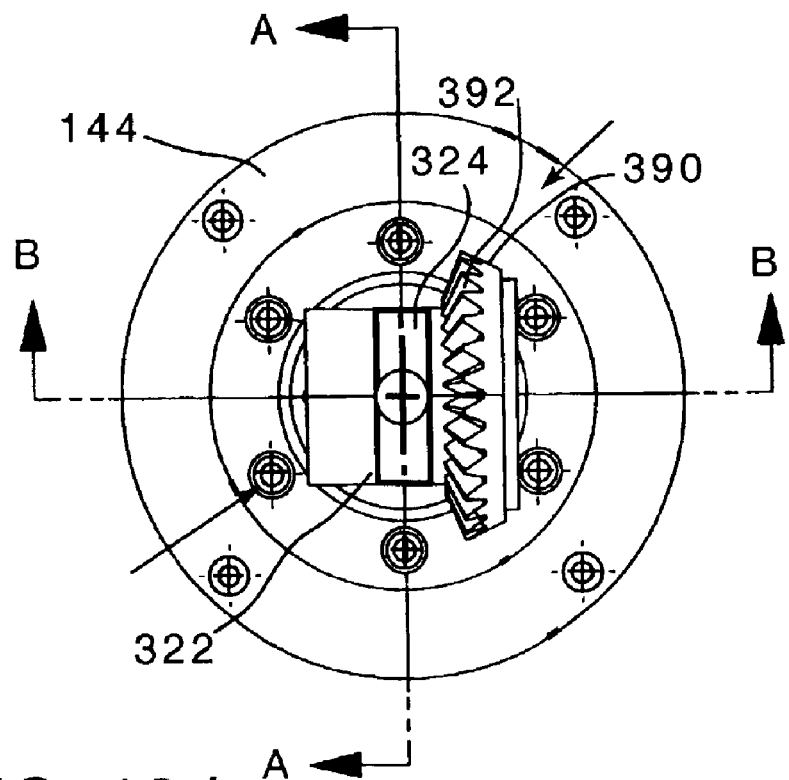
Figure 12E:
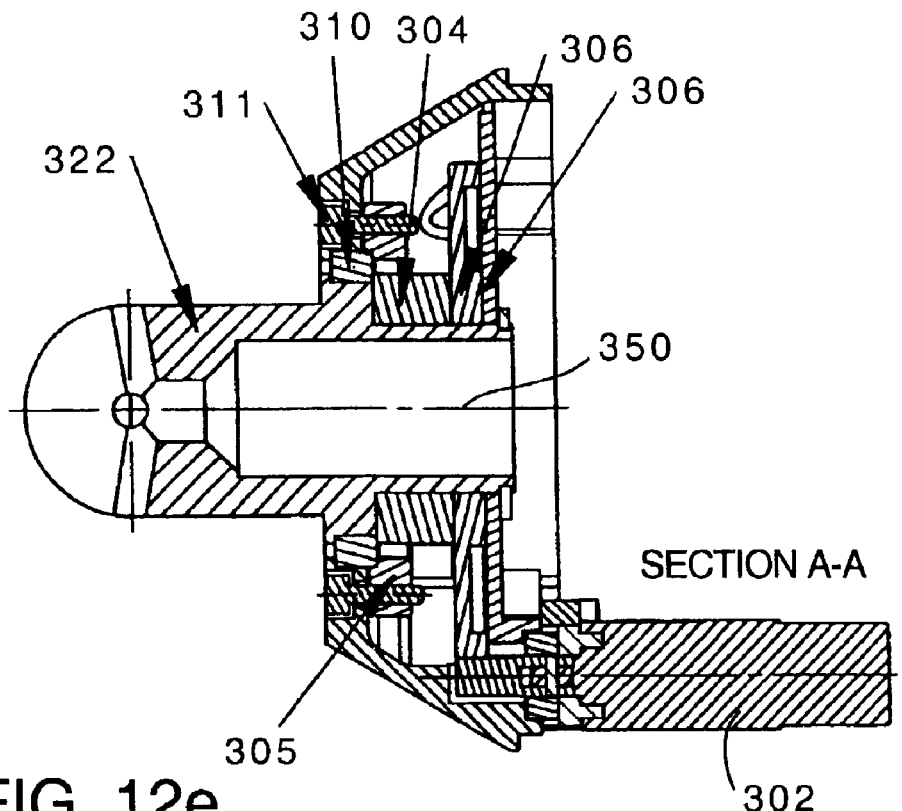
Figure 12F:
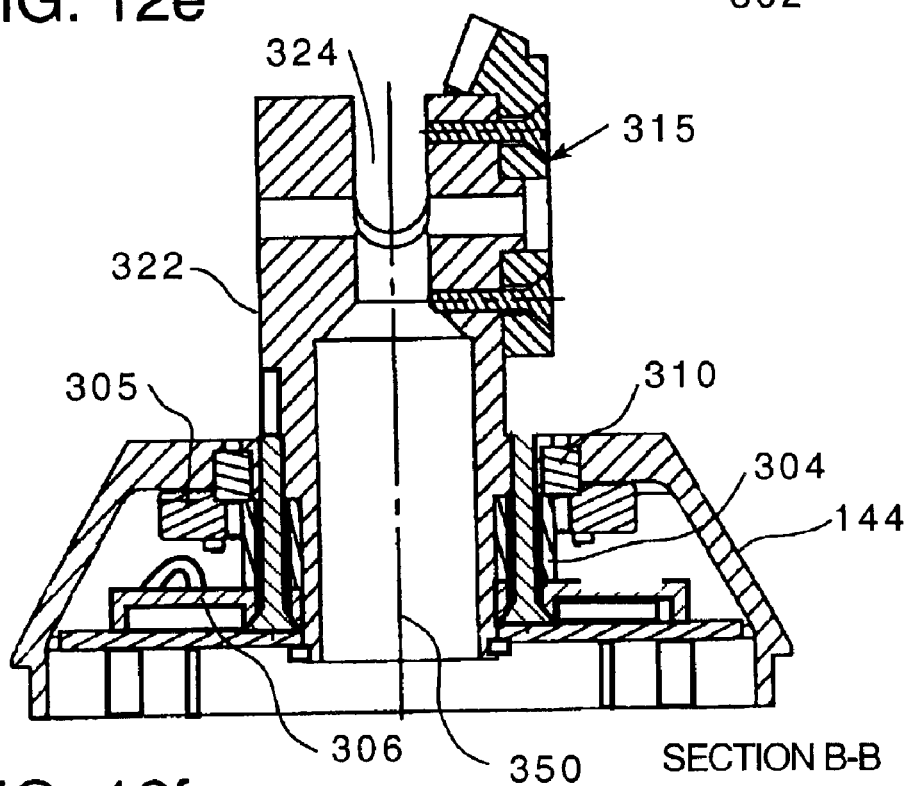
Figure 13:
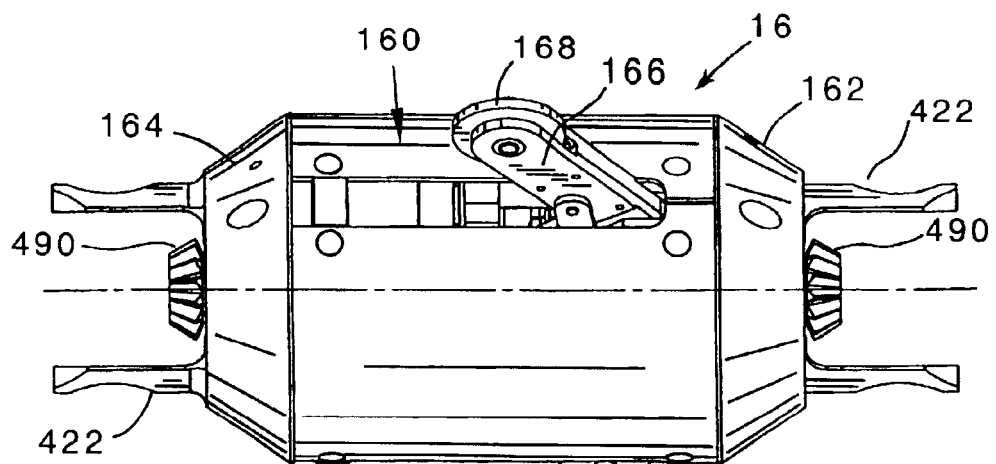
FIG. 13 illustrates an embodiment of the support module of FIG. 1.
Figure 14:
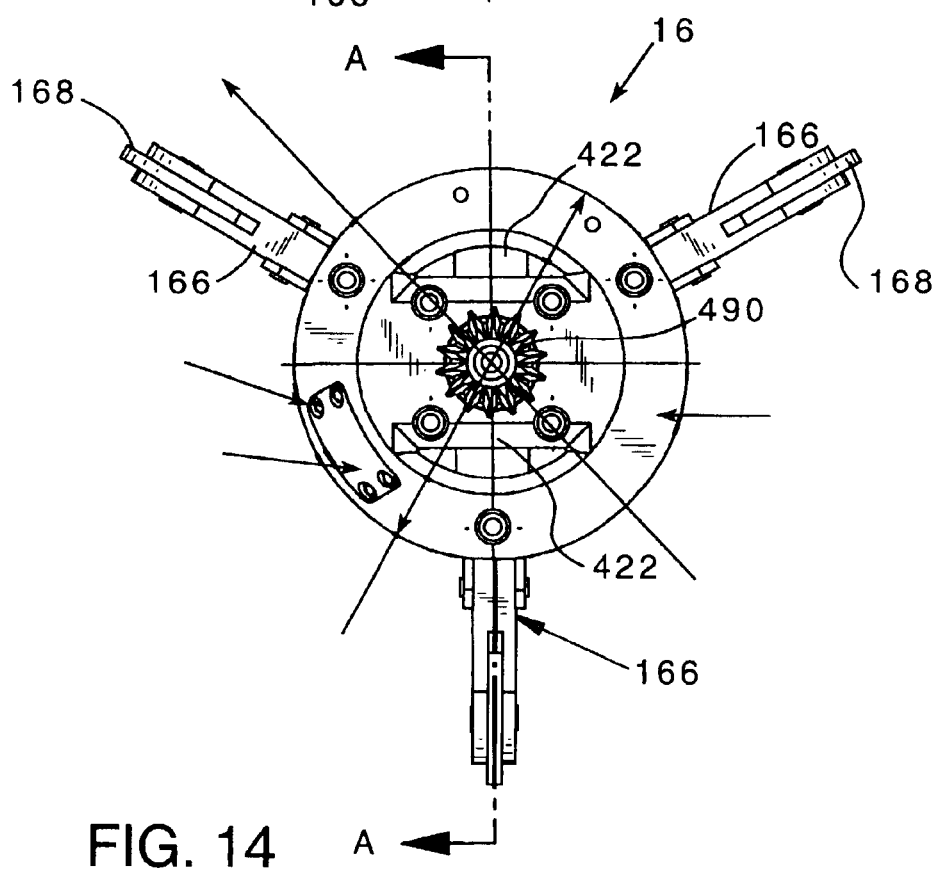
FIG. 14 illustrates an end view of the support module of FIG. 13.
Figure 15:
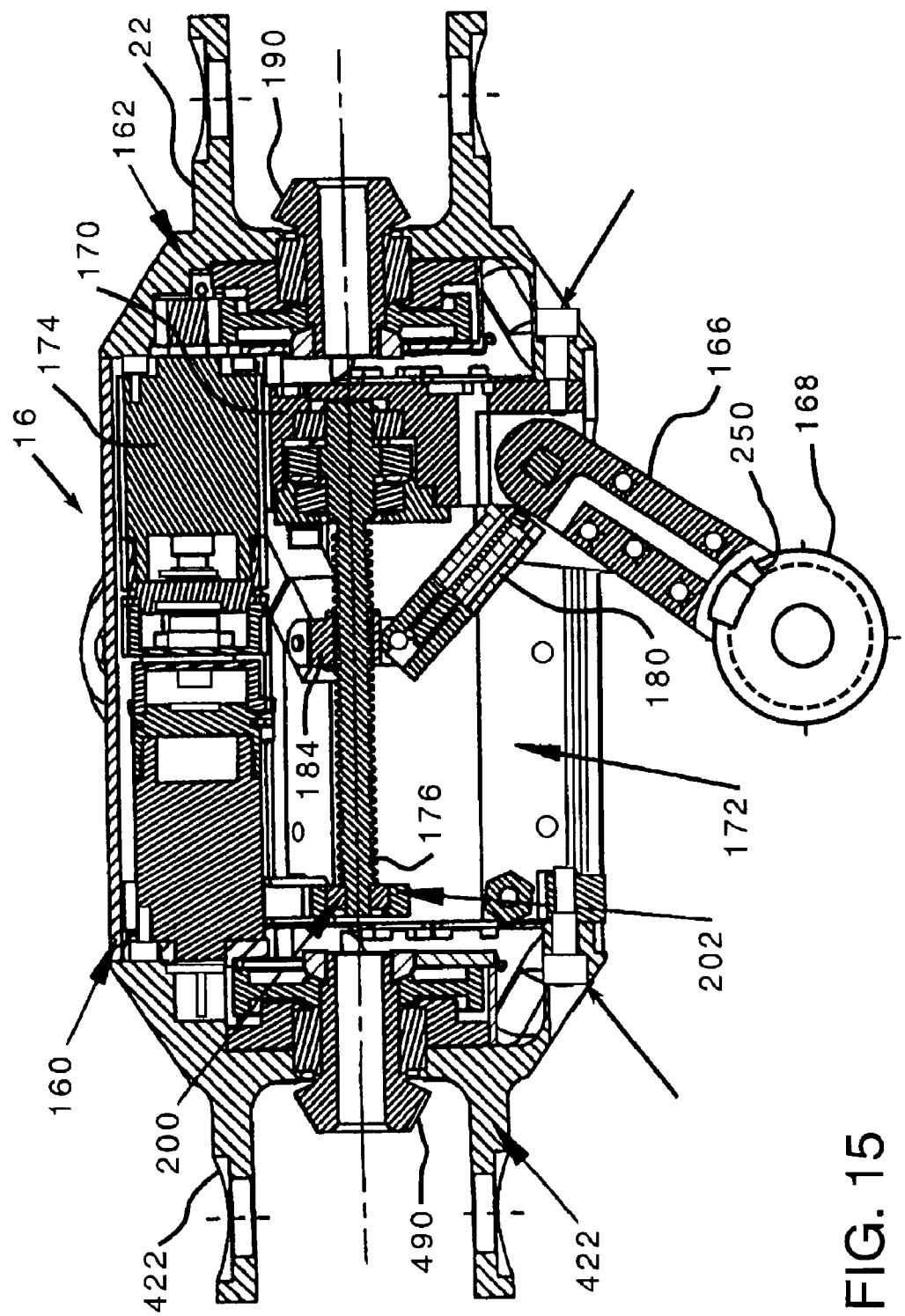
FIG. 15 illustrates a side section view of the embodiment of the support module of FIG. 13 through the line A—A of FIG. 14.

An embodiment of a power module 14 is shown in FIGS. 12A, B. The power module 14 includes a housing 140, first and second end caps 142, 144, and a second interconnect unit of the double-axis joint 20A at one end 144 thereof adjacent the drive module.

At end 144 of power module 14, as shown in FIGS. 12(C)–(F), a swivel block 322 is mounted in bearings 310 to the end 144 of the power module 14 by bearing retainer 305 with associated fasteners 311, or screws, 307 and bearing spacers 304 to permit swivel block 322 to rotate about the center line axis 350 of the power module. The bevel gear 390 is fastened to swivel block 322 by suitable fasteners 315. Rotation of swivel block 322 thereby causes bevel gear 390 to rotate. The beveled teeth 392 of bevel gear 390 mesh with complementary bevel teeth of bevel gear 90 on the end of drive module 12. Swivel block 322 includes an opening and open crevice 324 through which wires are ported from the power module to adjacent modules. The arrangement allows the wires to bend, but does not pinch the wires as the swivel block rotates and pivots.

A motor 302 in the power module 14, which is mounted offset from the centerline of the power module, drives the swivel block 322 through a reduction gear set 306. The axis of rotation of the swivel block 322 is parallel to, and preferably coincident with, the centerline 350 of the power module 14. The range of motion of the roll axis is plus or minus 180°. The first and second interconnect units provide a double-axis joint that allows movement in any plane and through any angle within the hemisphere of the joint.

The joint created by the coupling of the bevel gear teeth of gear 90 of the drive module 12 with the bevel gear teeth 392 of gear 390 of the power module 14 form a steerable universal type joint that allows rotation through 360° (+ or −180°) and movement through any plane within the hemisphere. The gears mesh to allow full rotation and the pivotal connections with the associated devises allow 180° (+ or −90°) movement through a plane. As the gears rotate relative to each other and the modules pivot, movement in any plane through any angle may be achieved, thereby allowing the system 10 to navigate any pipeline configuration. While the description and figures place the clevis mounts 22 on the drive module 12 and the swivel block mount 322 on the power module 14, the arrangement may be reversed.

There is a third interconnect unit at the opposite end 142 of the power module 14 which forms part of a single-axis motorized interconnect 20B. It forms a joint with a fourth single axis interconnect unit on the adjacent support modules 16. Similarly, the ends of each of the support modules 16 and adjacent ends of the electronics module 18 include one of the opposing third and fourth single-axis interconnect units 20B that allow rotation about the pitch axis only.

Each third and fourth interconnect unit 20B includes a fixed mounting clevis 222 and a bevel pinion gear 146. Each mounting clevis 222 includes an opening for receiving a pin to rotatably couple mounting clevis 222 to the adjacent devises 22 of the second interconnect unit 20B of the adjacent module to allow the adjacent modules to rotate (+ or −90°) relative to each other. The fixed, unpowered clevis mounts 222 are mounted in their respective end caps in the electronics module 18 and the ends of the 142 two power modules 14. Thus, the power module has one fixed clevis mount 222 and one powered swivel block 322. The electronics module has two fixed clevis mounts 222. The drive mechanism for the pitch axis of each of the single-axis motorized interconnects is the same as the drive for the double-axis described above. All of the motors and gearing for the single-axis interconnect units are located in the support modules 16. Each gear 146 of the third and fourth interconnect units 20B is the same as that described above, except that the clevis mounts 222 are fixed and do not swivel.

Only the terminal end drive modules 12 need to be steerable and bendable in all planes and angles to allow the drive modules to turn at sharp degrees and to travel. The modules in the middle of the system 10 are followers and need only bend in one plane. The middle, or mid-train modules may be rotated about the roll axis as a group by operation of both roll axis motors 302 in the power modules simultaneously, the drive modules being fixed within the pipe by their respective drive arms 52 and the passive arms 166 in each support module being retracted so as to permit rotation of the mid-train modules.

Each gear 146 is pivotally connected by a pin 148 to its associated fixed clevis 222. As shown in FIG. 12A, the gears on each end of the modules 14 are mounted to face in opposite directions to maximize maneuverability of the adjacent modules.

All axes of the steering system of the module train may have potentiometer feed back to provide absolute knowledge of each axes' position. Potentiometers are positioned at every moving part except the wheels. The idler wheels 168 carry encoders on them. Referring to FIG. 3, potentiometers may be positioned on the axis of 50.

The power modules 14 include a compartment 150 for containing a power source. The preferred power system for the system 10 robot is based on chemical energy-storage, namely batteries, such as a battery pack 152. The choice of the battery is driven by its use and energy and power-requirements. The battery selection may include, for example, nickel metal hydride (NiMh) and Li-Ion batteries. The compartment has end walls 154. The battery pack 152 may contain, for example, a plurality of batteries and battery contacts in sufficient number to provide the power necessary for desired inspection and data collection projects. For eight hours of substantially continuous deployment and collection and transmission of visual data, 40 NiMh battery cells, split into 2 packs having 20 cells per pack at about 1.2 volts per cell have been shown to be sufficient. The power supply is sufficient to allow operators to teleoperate or supervise the system operation in real time. For the standard 8 hours of operation, 24 volts are sufficient. That voltage can be provided by 4 Volt Li-Ion cells or 1.5 volt alkaline batteries, however, the latter type battery can not be recharged. Any appropriately sized power cell combination that will yield about 24 volts at a relatively high energy density of about 3800–4,000 milliamps per power cell will be sufficient to power the module train as described for 8 hours of work. Commercially available battery technologies, in terms of energy-density and power-capacity, may be used as the power source. Their volumetric density allows them to be packaged properly in the available space. Those skilled in the art will recognize that lithium batteries or other self-contained sources of stored power may be used. As mentioned above, power modules 14 may provide a pressurized environment if it is determined that the cells cannot withstand differential pressures of the environment in which the modules will be deployed.

FIGS. 13 through 17 illustrate an embodiment of the support module 16 of the inspection system 10. Support module 16 includes a housing 160 having end caps 162 and 164. A second interconnect unit 20B comprising a gear 490 and a pair of opposing clevis supports 422 is positioned at each end 162, 164. The bevel pinion gear 490 is oriented in a similar fashion to the bevel pinion gear 90 described above with respect to the drive module 12. However, the interconnect of the supply modules 16 are a single axis fixed interconnect. All motors and gearing for the single axes steering interconnects are housed in the support module 16. The beveled end projects from each end 162, 164 of the housing 160 between each pair of clevis supports 422 to mesh with the beveled teeth of the gear of the adjacent module, together forming a single axis, second interconnect joint 20B as described above.

Figure 18:
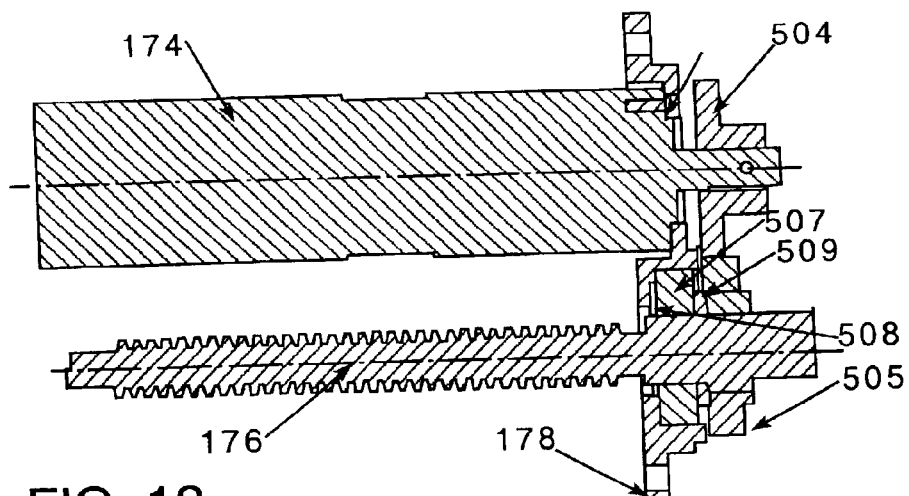
FIG. 18 illustrates a section view of the idler arm motor of the idler arm mechanism of FIG. 17.

The support module 16 includes a support arm mechanism 170 and an electronic component 172. Each support arm mechanism 170 includes a base 178, three passive arms 166, each having one wheel 168 at its free end, and an associated idler extension arm 180 to couple each such passive arm 166 to an extension shaft 176. The passive arms 166 are spaced at intervals around the housing 160. The housing includes openings to permit the wheel arms 166 to move inwardly and outwardly relative to the housing 160. An idler arm motor 174 is also provided. A section view of the idler arm motor 174 is shown in FIG. 18. Each idler extension arm 180 is pivotally connected at one end to an intermediate location on one of the passive arms 166 and at the other end to a nut 184 that rides on shaft 176. One end of each arm 166 is connected to a different wing 182 of base 178. The extension shaft 176 is connected at one end to a bearing 200 and end lug ring 202. The shaft 176 is connected at the other end to a bearing 507, spacer 509 and clip 508 within base 178. A gear pass 504/505 within the base operatively connects the idler arm motor 174 to the shaft 176. A potentiometer 520 (see FIG. 17) is mounted by cross pins to the pivot arm on the axis of the motor 174 to measure the angle of rotation of the arm. Each wheel 168 may include magnets and a magnetic sensor to detect the motion of the wheels. The sensors detect the number of partial rotations of each wheel 168 and the angle of rotation. Travel direction and travel distance are detected by use of quadrature encoders.

Sensors 250, such as wheel-follower odometers (encoders), may be positioned in wheels 168 and the passive arm 166 housing. At each wheel, a set of two hall-effect sensors and a set of magnets produce a quadrature signal to tell direction and distance. All six quadrature signals are weighted and averaged. This approach is very valuable in the case of slippage, turning, etc.

The electronics component 172 of support module 16, as shown in FIGS. 16A–C, includes a housing 190, a pair of circuit boards 192, and a plug and socket 194, 196. Electrical connections 198 are provided at each end. End caps 162 and 164 include wire access ports and associated port covers for passage of electronic communication wires through the module to adjacent modules.

Figure 20:
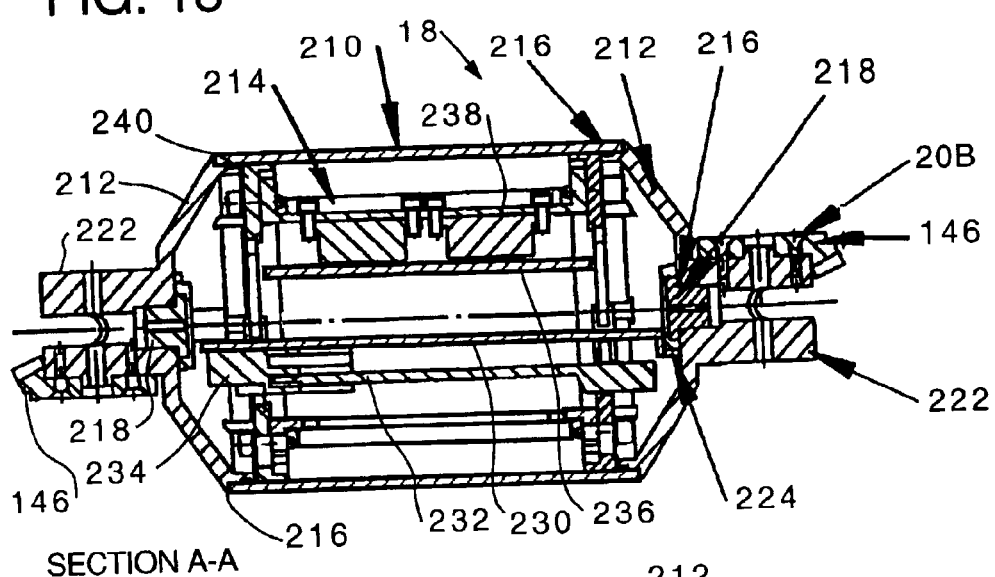
FIG. 20 illustrates a side section view of electronics module taken through the line A—A of FIG. 19.
Figure 19:
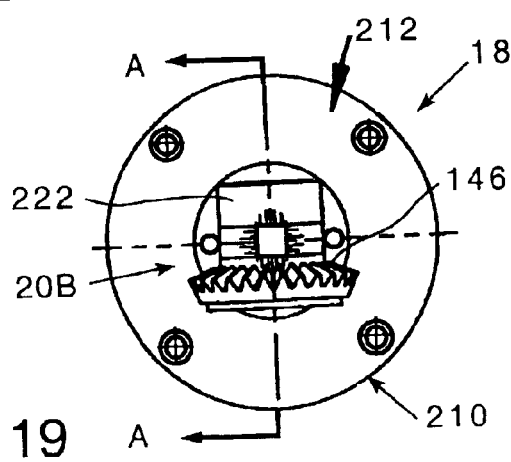
FIG. 19 illustrates an end view of an embodiment of an electronics module of the inspection robot of FIG. 1, showing the single axis interconnect.

The electronics module 18 is, in the embodiment of FIG. 1, positioned in the middle of the train-like configuration of the plurality of modules. Referring to FIGS. 19 and 20, electronics module 18 includes a housing 210, the system's on-board computing components 214, and end caps 212 including a rolling unit 20B comprised of clevis mount 222 at each end with the associated gear 146. Standard O-rings 216 are provided to seal the interior of the electronics module 18 against gas leakage from the pipe. A feed through conduit 218 and retainer 224 are provided to permit electronic connection to other modules. Bundles of wires run through the entire train of modules, through openings in each interconnect unit to the electronics module.

Referring to FIG. 20, the electronics components of electronics module 18 may include CPU card 230 and wireless network communications card 232 (such as a wavelan/IEEE 802.11b card) in a support bracket 234, and power conditioning circuit board 236 and DC-DC converter 238 held in support ring and ring bracket assembly 240.

There are three levels of computer architecture in the system 10. The processor in the electronics module 18 processes image data received from the cameras, communicates with the user interface via a wireless Ethernet, and commands the other modules, 12, 14 and 16, to execute various tasks via a control area network bus. The computer architecture is described in more detail below.

The computing system required to support the high-end digital imaging, dewarping and mosaiquing software, as well as all the motor-controller, communications and other I/O and house-keeping and monitoring tasks, is preferably of a processor-power level. Such processors exist in comparable levels as embedded-system OEM board-sets, sized to a PC-104 format, which is in essence a 3.5"-square stack of cards.

A customized CPU board-set centered around a low-power high-end processor comparable in computation performance to a Pentium-I class processor, similar to those in use with handheld and palmtop computers may be used in the system 10. The configuration freedom thus obtained allows the board-set to utilize the latest in chip technology and I/O and digital electronics.

Figure 21:
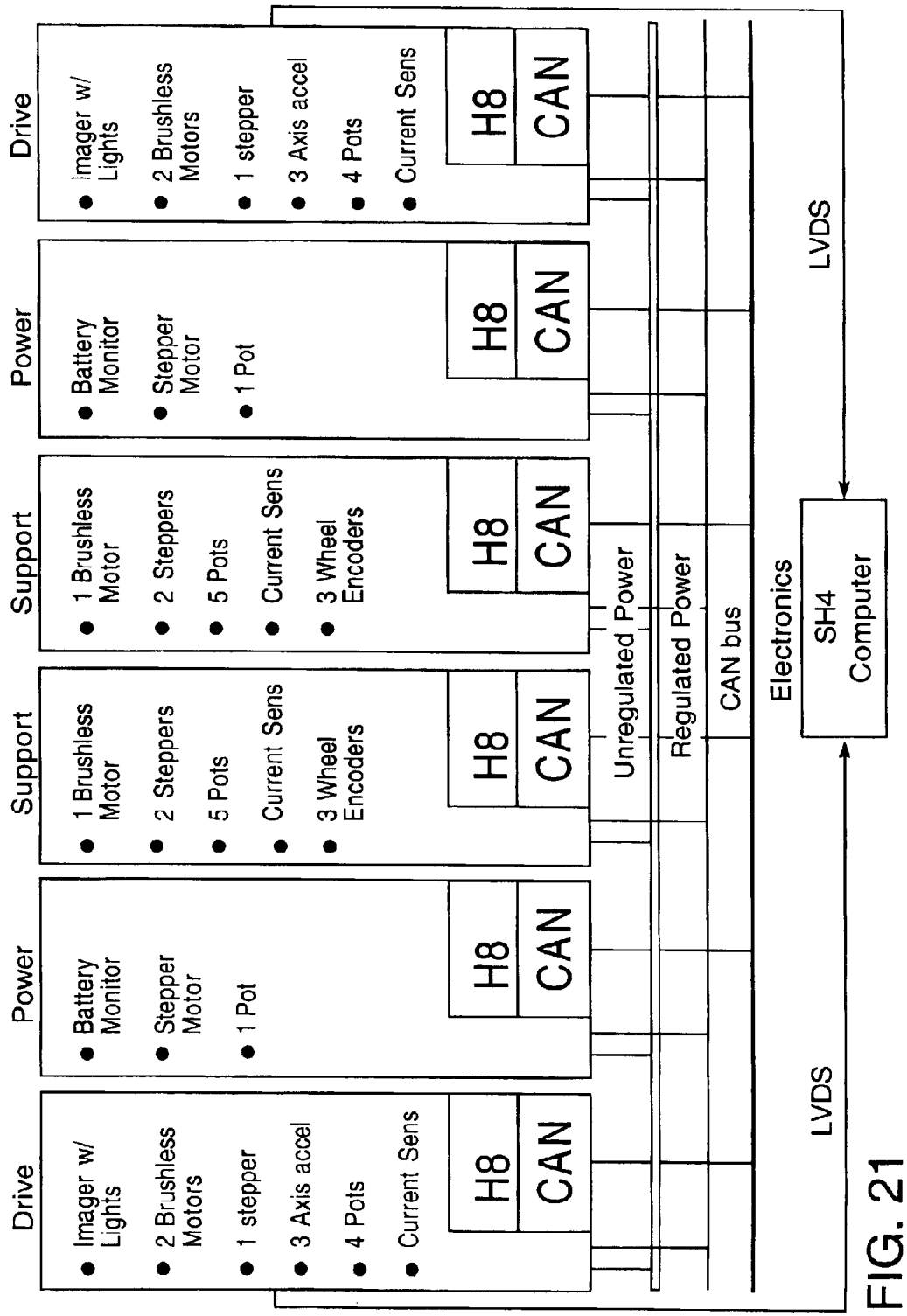
FIG. 21 is a representation of an embodiment of the distributed computer architecture of the electronics module.

The computer architecture may be based on a typical embedded-CPU hierarchy, whereby all associated peripheral hardware is interconnected to the central processor over a control bus such as, for example, a CAN (control area network) bus. FIG. 21 is a diagram of the communication architecture of the system 10 according to one embodiment. As illustrated in FIG. 21, a control bus, such as a CAN bus, may communication control signals from the central electronics module 18 to the other modules 12, 14, 16. The electronics module 18 may, for example, communicate to the other modules 12, 14, 16 instructions to execute tasks via the control bus. The tasks may be, for example, scripted tasks such as, for example, steering tasks.

Figure 27:
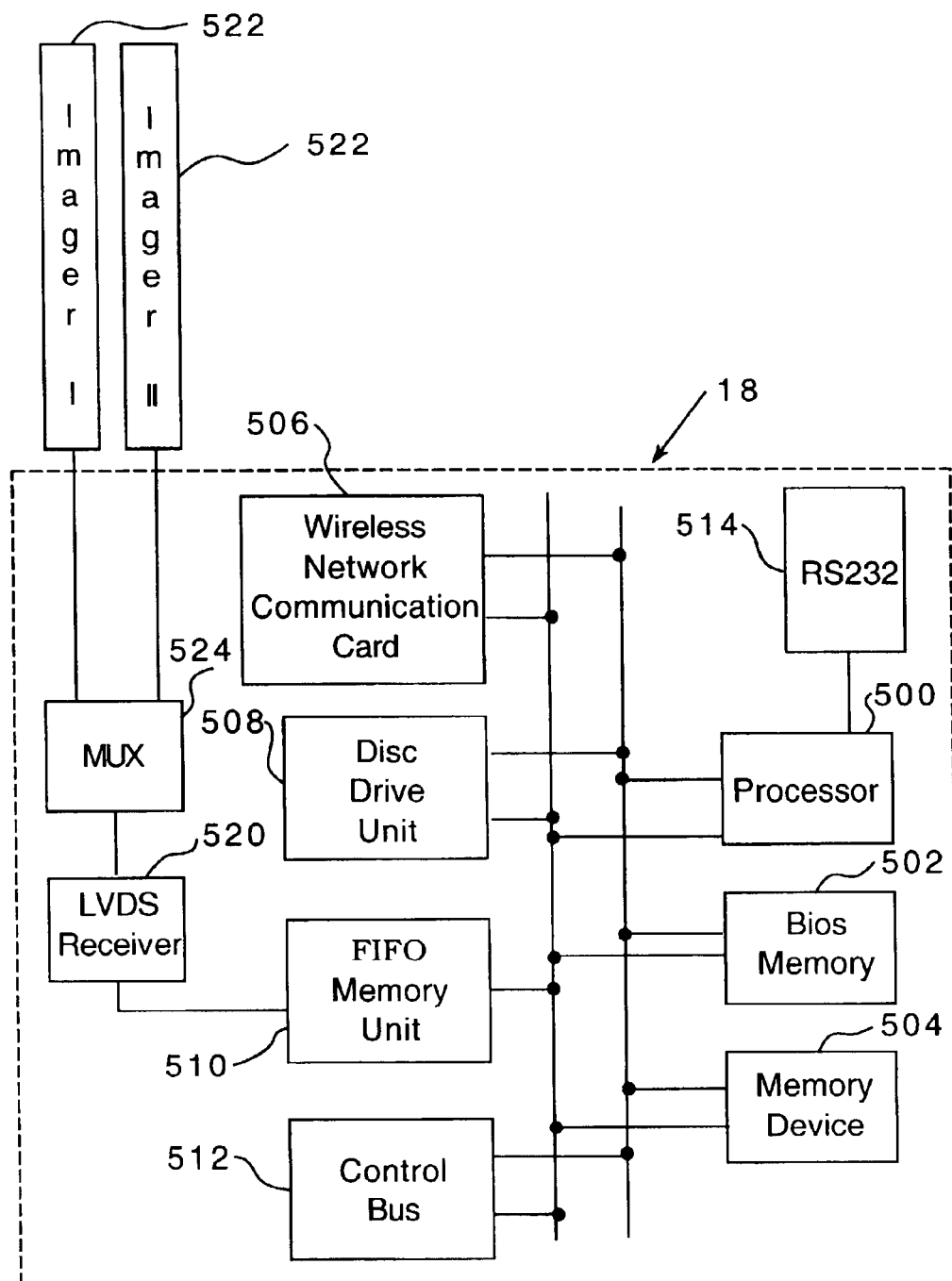
FIG. 27 is a diagram of an embodiment of computer architecture that may be used for a processor used in the system of the present invention.

FIG. 27 is a diagram of the hardware components of the central electronics module 18 according to one embodiment. As illustrated in FIG. 27, the electronics module 18 includes a processor 500, a BIOS memory unit 502, a memory device 504, a wireless network communication card 506, a disk drive unit 508, a FIFO memory unit 510, a control bus 512, and a RS232 port 514. The processor 500 may be, for example, a Hitachi SH4 or similar processor. The BIOS memory unit 502 may be implemented, for example, as a programmable read only memory (PROM). The memory device 504 may be implemented, for example, as a synchronous dynamic random access memory (SDRAM) unit. The wireless network communication card 506 may enable wireless communications with the user interface via, for example, a wireless LAN. According to one embodiment, the wireless network communication card 506 may employ the IEEE 802.11b standard. The disk drive unit 508 may be, for example, a hard disk drive (HDD) unit. The FIFO memory unit 510 may be any memory device that is configured to retrieve data stored for the longest time. The control bus 512 may be, for example, a CAN bus, as described previously to communicate control signals to the other modules 12, 14, 16 of the system 10. The RS232 port 514 may provide a serial data port for, for example, facilitating debugging of the electronics module 18. According to one embodiment, the hardware components just described, i.e., the components 500, 502, 504, 506, 508, 510, 512, 514 may be co-located on one PC board.

As illustrated in FIG. 27, the control electronics module 18 may also include an LVDS (low voltage differential signaling) receiver 520 in communication with the imagers 522 of the drive modules 12 via a multiplexer 524.

Low Voltage Differential Signaling is a low noise, low power, low amplitude method for high-speed (gigabits per second) data transmission over copper wire. LVDS differs from normal input/output (I/O) in a few ways. Normal digital I/O works with 5 Volts as a high (binary 1) and 0 volts as a low (binary 0). When you use a differential, you add a third option (−5 Volts, e.g.), which provides an extra level with which to encode and results in a higher maximum data transfer rate. According to one embodiment, LVDS means that the standard 5 Volts is replaced by either 3.3 Volts or 1.5 Volts. LVDS may use a dual wire system, running 180 degrees of each other. This enables noise to travel at the same level, which in turn can get filtered more easily and effectively. With standard I/O signaling, data storage is contingent upon the actual voltage level. Voltage level can be affected by wire length (longer wires increase resistance, which lowers voltage). But with LVDS, data storage is distinguished only by positive and negative voltage values, not the voltage level. Therefore, data can travel over greater lengths of wire while maintaining a clear and consistent data stream.

LVDS transmitters (not shown) at the drive modules 12 may serialize the data from the digital imagers 522 and transmits the serialized data to the LVDS receiver 520 of the central electronics module 18.

The LVDS receiver 520 may receive pixel data from only one of the imagers 522 at a time due to the multiplexer 524. The LVDS receiver 520 may receive serial pixel data from one of the imagers 522, and deserialize by, for example, converting it back to a TTL/CMOS signal. Deserializing the data allows the pixel clock data to be extracted. The deserialized image pixel data may be stored in the FIFO memory unit 510. The FIFO memory unit 510 may send, for example, a direct memory access request (DMA) to the processor 500. Once the processor 500 acknowledges the DMA request, the image pixel stored in the FIFO memory unit 510 to the memory device 504, which, as described previously, may be a SDRAM device. The processor 500 may then compress the image, code it with, for example, odometry data, and package it in an data packet, such as an Ethernet or IP packet. The packetized data may then be transmitted by the wireless network communication card 506 to the remote user interface by a wireless data network, such as an IEEE 802.11b network.

Figure 25:
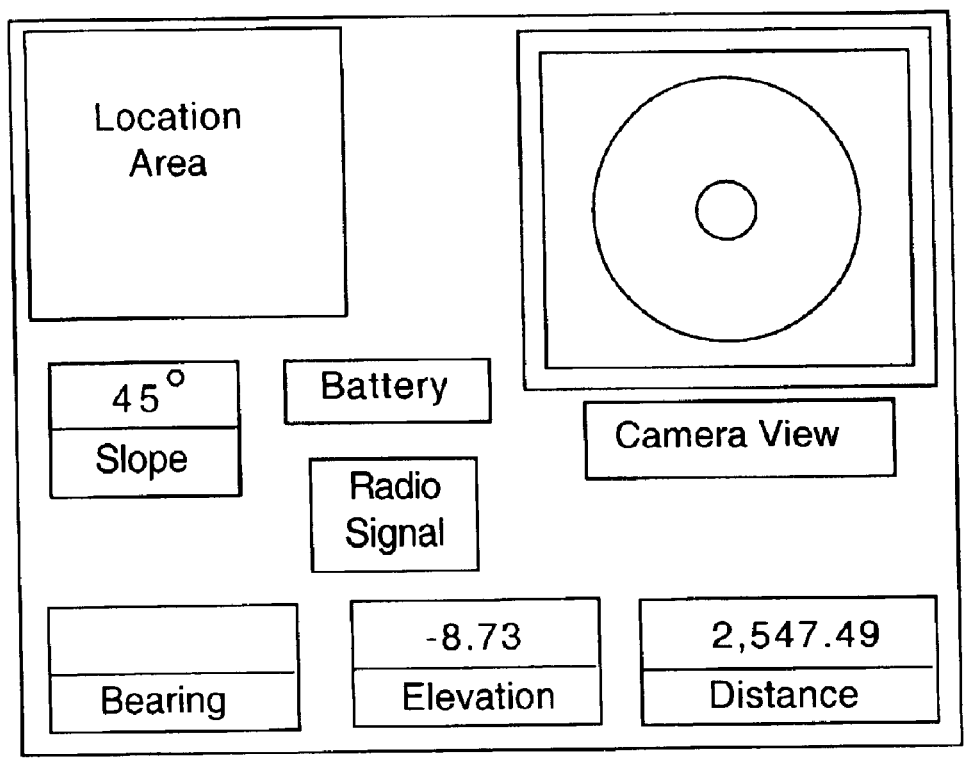
FIG. 25 is an embodiment of an operator interface screen for displaying received data transmitted from the inspection robot of FIG. 1.
Figure 26:
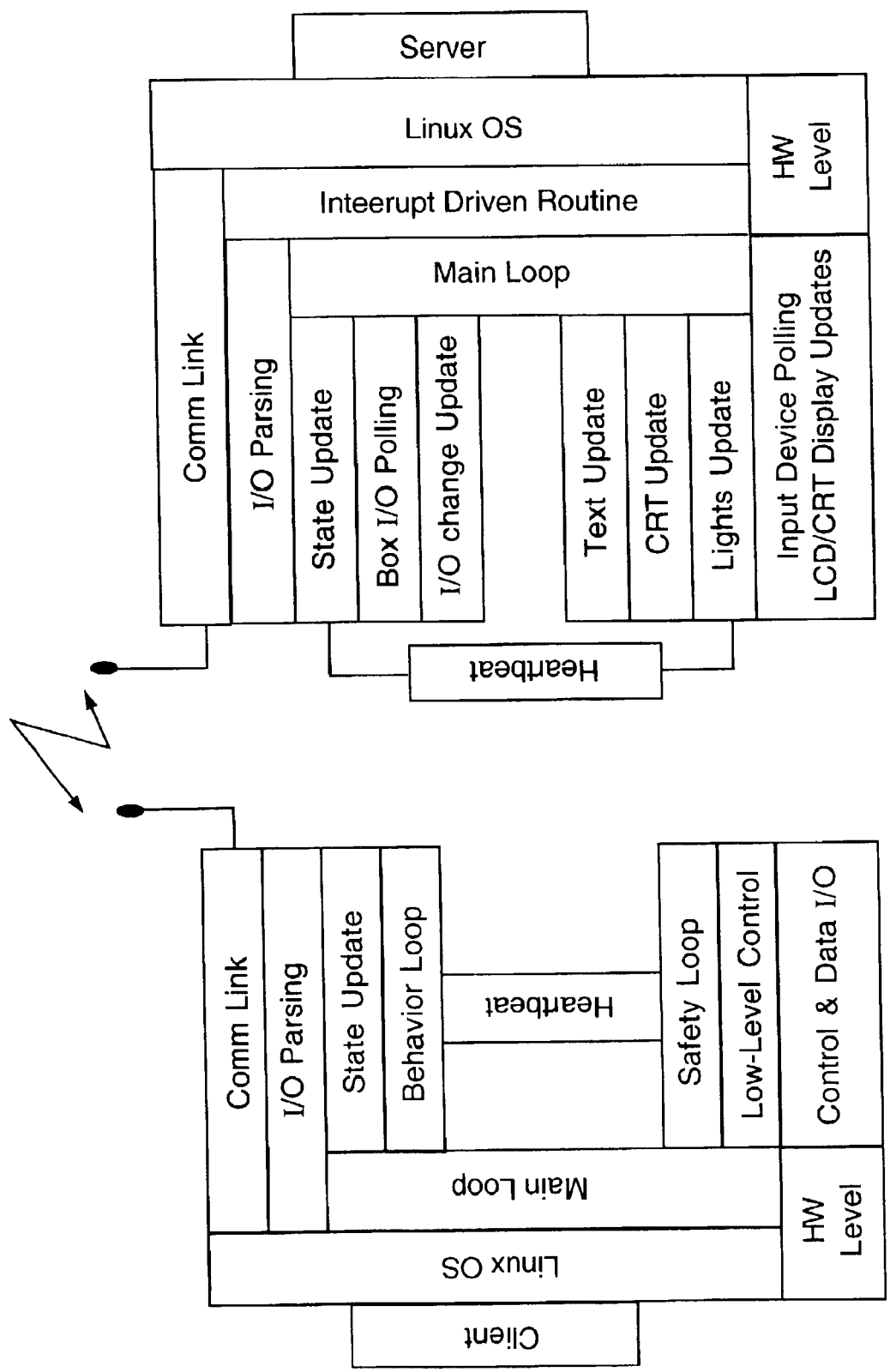
FIG. 26 is a diagram of an embodiment of software architecture that may be used for operations of the system of the present invention.

As illustrated by the display screen shown in FIG. 25, all operations are viewable and controllable in real time from a single console by a single operator outside the main, plugged into the system only by virtue of a cable to an antenna sticking into the main. As described previously, data from the system 10 may be transmitted to the remote operate via a wireless communication link.

In addition, the computer-interface may employ other distributed processor-boards in each module, for example, Hitachi-style boards based on their 16-bit H8 family, which communicate the SH4 via a common bus (I2C, RS-422, CAN, etc.), and execute high-speed commands locally. In addition, the use of a digital imaging camera, with a dedicated high-speed digital bus.

The software architecture is detailed at a high level. The main premise is that the on-board system 10 computer would be a 'client' to the outside computer in the operator control box. The operator control box would provide for a continuous loop, whereby all input-devices (joysticks, camera-pointers, light-buttons, etc.) may be polled, status messages written to a textdisplay and all digital video displayed in raw and dewarped fashion. A communication data-parser that transmits and receives data-packets over the wireless Ethernet link may be used. The entire software may operate under the Unix®-like real-time operating system LINUX®, allowing real-time operations without substantial overhead. The on-board architecture would be almost identical to that described earlier, except that additional on-board communications, safety/health code, and other exception-handling software would be running in the same main loop. The hardware interface and control structure of the software may be defined at two levels, namely at the main and central processor level, and then at the individual distributed processor-levels within each module. An embodiment of the software-architecture design is shown in FIG. 28. All software may be written in any computer language now known (e.g., C, C++, visual basic, etc.) or hereafter developed.

The communications system may be based on existing commercially available components developed for wireless communications in the computer-market. Current wireless networking technology, allows for the use of 2.4 GHz radio-frequency transceiver systems in the form of a PCMCIA-card, implementing a software protocol (Ethernet) and hardware-handshaking interface (error correction, collision-detection, etc.) developed by Institute of Electrical and Electronics Engineers (IEEE) (IEEE 802.11 b), capable of generating communication-bandwidths on the order of 11 Mbps over short ranges (300 feet with omni-directional antennae), and reduced rates of 1 Mbps over longer ranges (in the order of 1200 feet with omni-directional antennae); use of directional antennae inside pipes should yield even higher ranges.

The computer and telecommunications/cell-phone industries will continue to push communications into ever-higher bandwidths to allow the transmission of more data and the access of more users. This increase in bandwidth will help the utility industry in the same way (increased data and access-clients). Those skilled in the art will recognize that for each pipe diameter, there will be an optimum frequency to produce the maximum range for communication. The advantage in using established communication protocols is that the system 10 can be upgraded to this higher bandwidth literally by simply exchanging the above-shown LAN-card in the electronics module 18.

Figure 22:
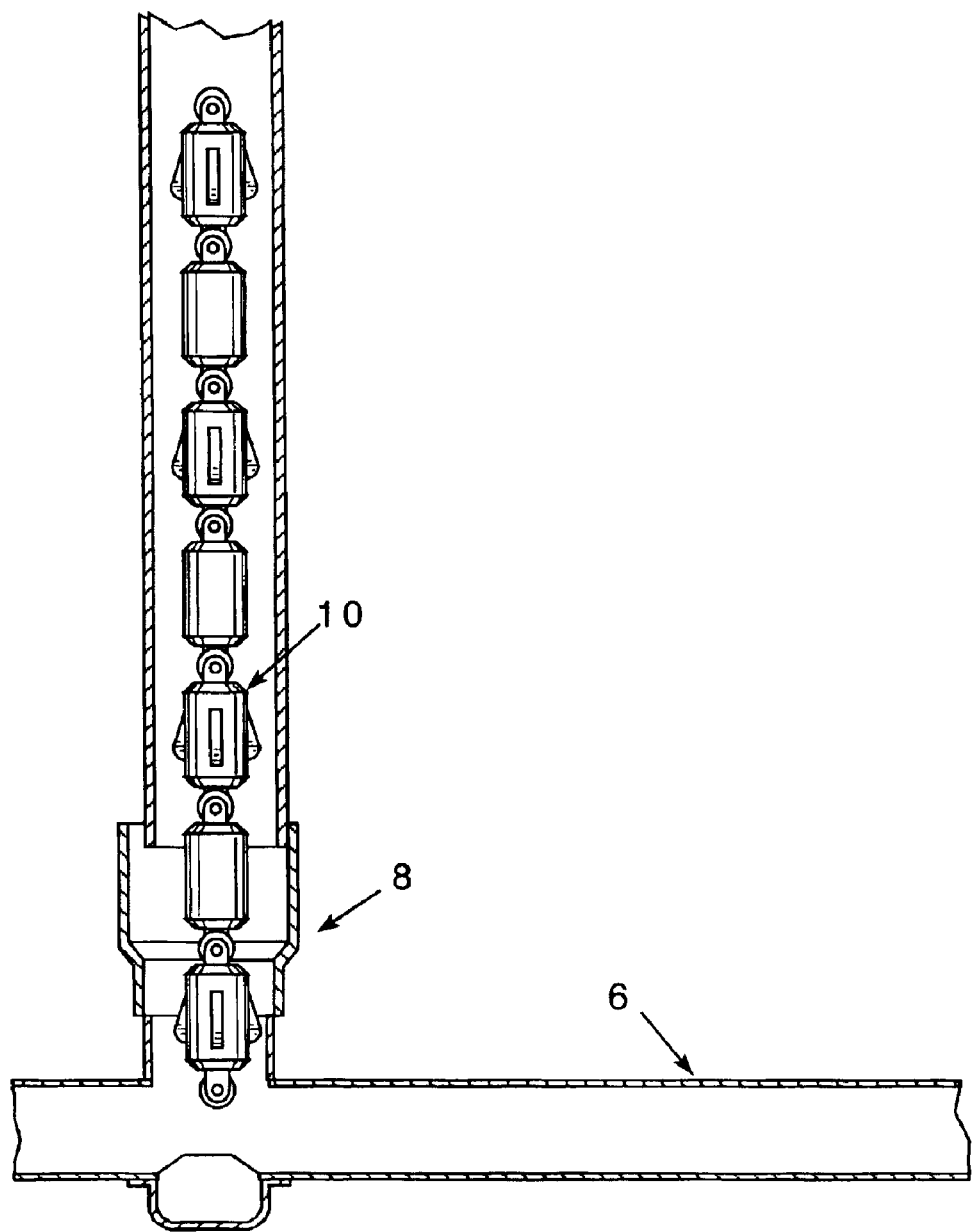
FIG. 22 is a view of the inspection robot of FIG. 1 entering a pipeline.
Figure 23:
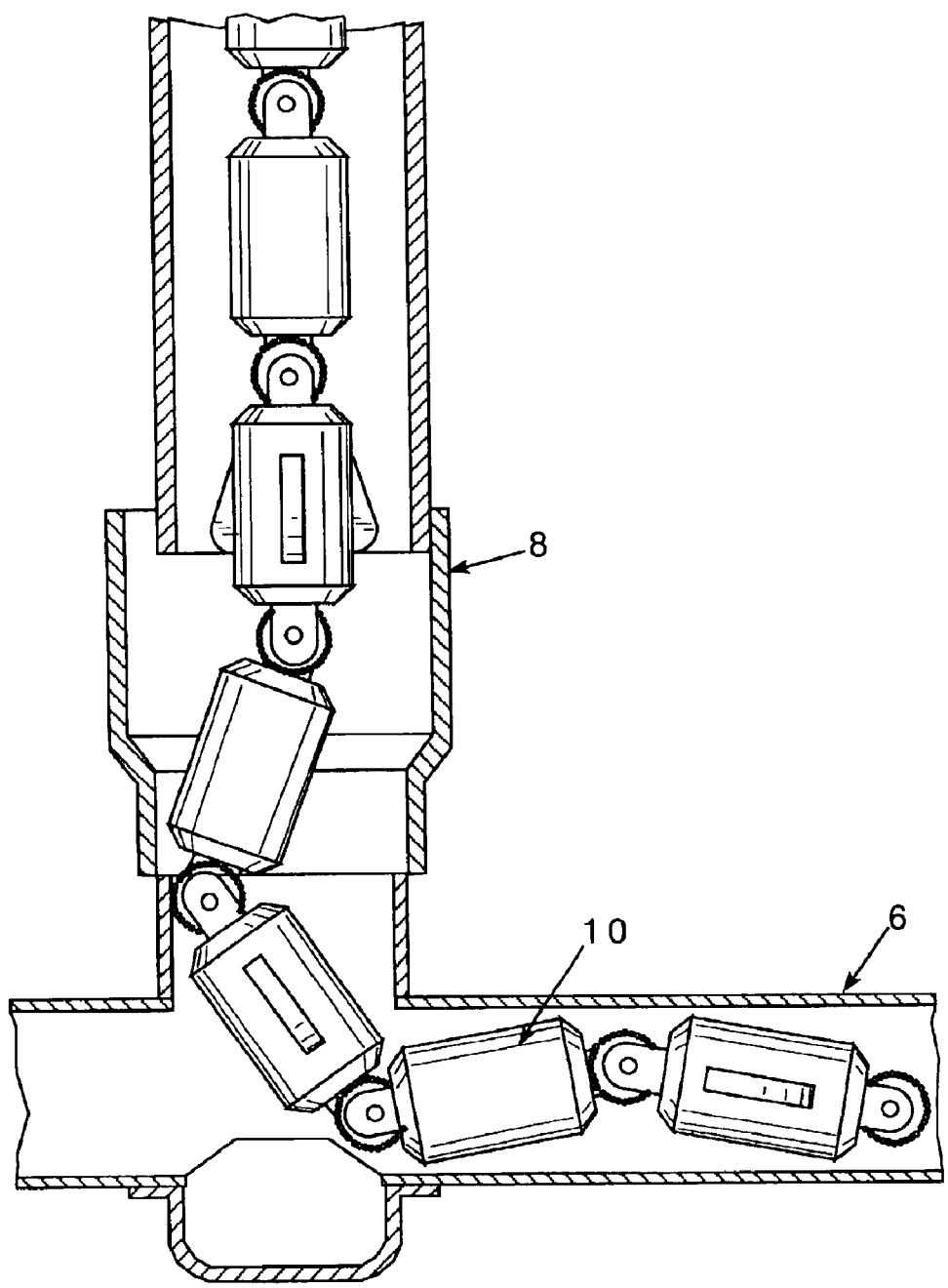
FIG. 23 is a view of the inspection robot of FIG. 1 making a 90° turn into the pipeline.
Figure 24:
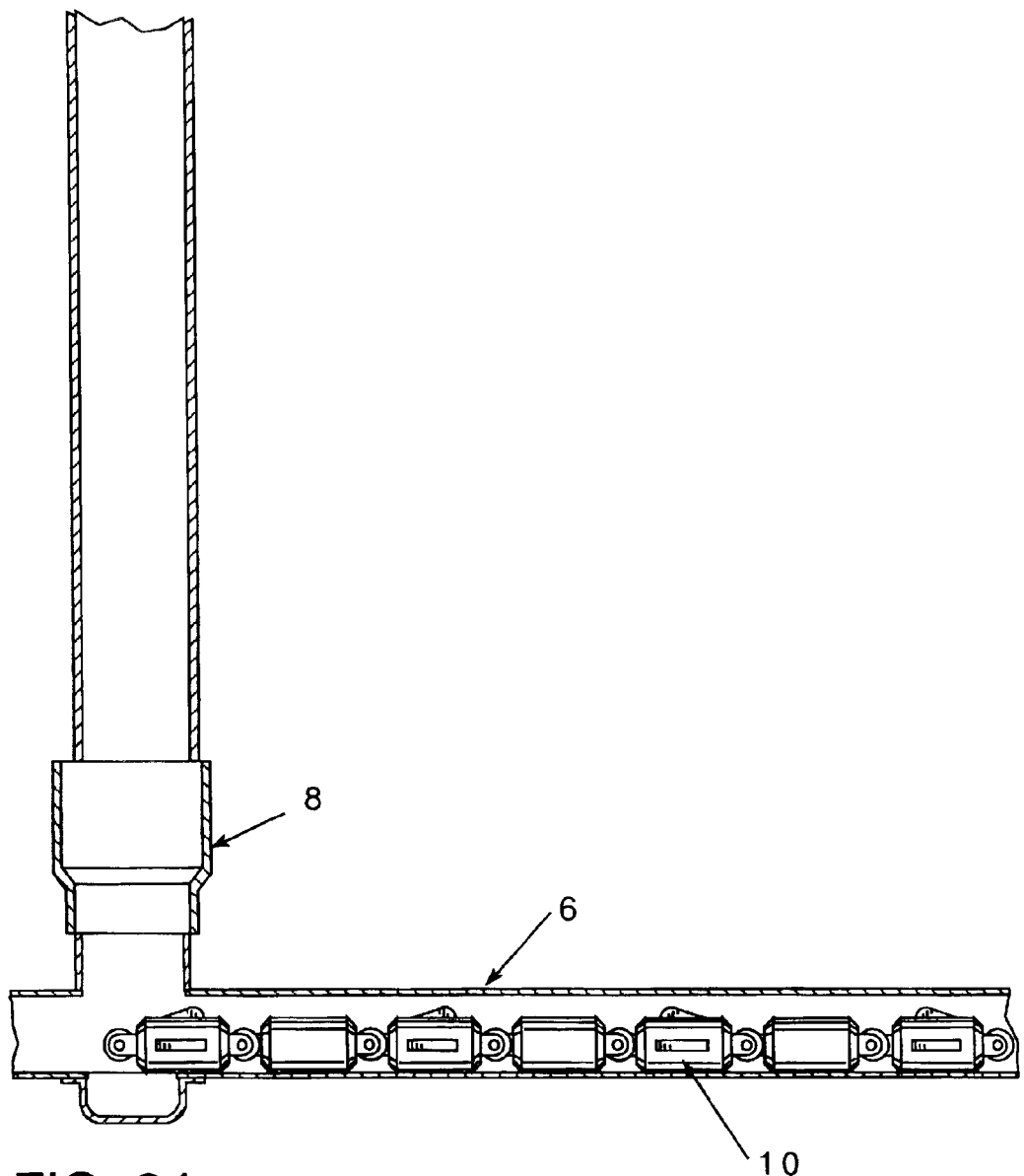
FIG. 24 is a view of the inspection robot of FIG. 1 after it has entered the pipeline.

The system 10 may be deployed through a welded-on launch-chamber sleeve-system, shown in FIGS. 22, 23, and 24 on an excavated underground gas line into the live environment. A commercially available pipe-access system, for example, from Mueller, Inc., may be used to launch the system 10. The launch system consists of two half-pipe diameter cast-fittings that are welded onto the outside of a pipe that has been unearthed. The flange-fitting on the top-section then receives a gate-valve, atop which can then be placed any other tool of choice. In order to make a full-diameter hole (hole the size of the pipe-inner diameter), requires a boring-tool that has a hydraulically-powered shell-cutter that is advanced onto the pipe and cuts both the top and bottom of the pipe, leaving the coupons (cut-out sections) to drop into the belly of the bottom-half of the welded-on fitting. Once an access-hole exists, the gate-valve isolates the pipeline from the launch-chamber that is used to launch the module-train into the pipe.

The launch-chamber, which may be a custom-fabricated system, need only be a simple hollow-pipe, that has a hook and recharge-port in the top, as well as an antenna- and power-hookup for the robot recharging and wireless communications. The antenna itself is mounted internal to the chamber on a deployment-carriage, allowing its deployment and orientation into the center of the live pipe, once the module-train is deployed. It will be appreciated that other launching systems, such as, for example, an angled launch chamber may be employed.

The system 10 adapts its geometry and locomotors to the encountered gas line internal diameter and moves down the pipe with speeds up to 4 inches per second by extracting power from its battery-pack. The on-board camera transmits live imagery. The system may communicate live TV and teleoperator control-data back/to the operator/receiver via RF using the pipeline as a waveguide. The system can reconfigure itself to access 90° bends, negotiating 1.5 D bends, with reduced travel and communication-link range. With a power supply of just 40 NiMh batteries, or any other suitable, preferably rechargeable power source, the system 10 can travel up to 2,500 feet+ in either direction from the insertion point, subject to communication-range and power-drop and recharge times. Deployments could last longer and go further depending on prevailing gas-flows, number of access-points and power supply. The power supply is calculated based on the distance of desired travel on a single charge and the communication links within that range. The simplest and most accurate 'navigation' approach to use is to visually count joints and software-reset the on-board odometer at each joint, measure each pipe-section individually and accurately, thereby generating a non-drifting estimate of longitudinal displacement within the pipe. The operator controls the movement, including the direction and speed, of the module-train by observing in real-time the images communicated from the on-board camera. The operator will know where the next bends and turns are in the pipeline based on the utilities internal records, and will instruct the train where to go next according to a predetermined "script". The directional "script" for a particular operation may be planned in advance and/or stored on the operator's PC. Alternatively, the operator may manually control the movement of the module-train in response to the images and circumstances communicated to the operator.

The on-board processor system may also be responsible for monitoring proper operation of all systems, determining the health of individual components and subsystems, as well as maintaining an estimate of navigational self-awareness.

The system 10 may utilize several schemes to monitor its own operation on-board, its health and communication link with the topside operator. The following modalities and schemes may be utilized:

At the highest level within the system 10, the individual distributed processor boards within each module, may communicate with the central processor over the common data-bus, acknowledging their presence and proper operation on a frequent basis—this is referred to herein as establishing and maintaining a 'heartbeat'.

The 'heartbeat' concept is taken a further step by the central processor, in that it establishes a regular communications interval with an off-board wireless control-box utilized by the operator. The idea is to ensure that the system 10 does not drive out of communication range unexpectedly. This can be detected by having the operator-interface computer send a regular 'heartbeat' signal to the system 10, which would be expected and answered by the same. Should it not receive the signal, the system 10 may be programmed to stop and execute a backup-maneuver to the spot where it was last known to have had bi-directional communications; this is an autonomous safeguarding behavior referred to herein as 'comm-reacquisition'.

In the case of the drive-module 12, the local processor may monitor motor-current and voltage, establishing the baseline of operation. Depending on the mode in which the system 10 might be (horizontal v. vertical, straight-v. turning), the local processor can safeguard the motor, but be overridden by the central computer. The localized three-degrees of freedom accelerometer signals also help qualify the system mode to allow the local processor to decide as to whether the current falls within the expected performance range.

The condition of the power pack may be monitored by use of a coulomb counter, which measures the charge used and the initial charge of the battery. A dedicated processor-board or task on-board the power-module local-controller may be responsible for monitoring pack-voltage, -current and -temperature. This is useful (but not required) to safeguard the pack from improper operation, and to allow the central The processor may compare pack voltage with a look-up table based on a discharge graph of the cell provided by the manufacturer; a measurement that allows the computer to alert the operator and only allow motions that bring the system back to its deployment point (under the current round-trip deployment model).

Safety-sensors that may be included in each module include, for example, moisture-detectors and oxygen-monitors. Each of these are simple implementations that allow monitoring the module-internals for the concentration of oxygen within each module, and open-circuit pins that if short-circuited by water migrating into the module, will alert the system and alert the operator to retrieve the system and initiate a shutdown as soon as possible.

The navigation scheme for system 10 uses multiple sensing-modalities to generate an estimate of the actual robot position within the pipe network.

The simplest, yet most error-prone open-loop measurement is based on encoding the drive motors by utilizing the hall-effect feedback to generate up/down counters that generate an estimate of progress-distance through gear-ratios and wheel-diameters. This measurement is inaccurate in that the wheels might slip with respect to the pipe-wall, and the outer diameter of the wheel is not constant due to compressibility of its urethane rim.

The next stage of encoding is based on the use of the centralizing wheeled-arms at each support module, to compute an 'averaged-out' estimate of travel along the pipe, utilizing their phased hall-effect encoders measuring distance as a function of wheel-rotation. This is especially important as the system makes turns and drive-wheels lose contact with the wall and we have to rely on rearward wheels and drives to update the position estimate.

In order to quantify travel as a function of three-dimensional distance, each drive-module may contain a three-degree of freedom accelerometer sensor that allows the computer to resolve the actual motion of the system 10 as to horizontal and vertical distance traveled. Gyros may also be used for this purpose. The drive arms are pre-loaded to provide adequate traction for the wheels. The current that is needed to drive the module train is measured. By knowing the torque current transfer function of the motor and the geometry of the arms, one can back calculate the normal force that should be applied to the pipe walls to achieve the traction needed to move through the pipe. Maximum force is not required at all times. More will be required for vertical or upwardly inclined movement and less for relatively flat travel. The force needed, for example, to move the robot up an incline or through a length of pipe is determined by determining the angle of the module train relative to gravity using an accelerometer as an inclinometer to determine the slope relative to gravity. It can be determined if the angle of incline has changed, and if the drive arms need to be preloaded more or less.

Lastly, each of the steering joints may be encoded with an absolute position potentiometer, allowing the motions to further be resolved within pipe-coordinates by the computer.

The explosive range for natural gas (NG) sits at about 14% to 17% natural gas (95% methane) by volume in an air-to-NG mixture. Operation outside of this arena, despite the presence of oxidizer and an ignition-source, will not cause an explosion. Given the above considerations the system 10, when used in natural gas pipelines, can avoid the use of pressurized enclosure wherever possible.

In the case of the drive/locomotion module, this implies, leaving the module 'open' to ambient conditions and ensuring, through seals and booting, that no foreign matter can get entrapped in the mechanism or water gaining access and allowing the short-circuiting of any electronics. Electronic elements at ambient pressure may be pressure-tolerant (up to 125 psig) and may be capable of operating in a pure natural gas environment.

The steering joint is inherently unsealable, except for allowing a boot to seal out foreign matter. All motors may be capable of operating within the pressurized natural gas environment.

The computing-module may optimally be hermetically-sealed to the outside environment, with the addition of two opposing one-way check-valves, enabling pressure-equalization to ambient conditions, with just a simple cracking pressure differential inherent in the check-valve. Hence all internal components may operate within a pressurized natural gas environment. The computer module may be purged of all air, and have the contents replaced with nitrogen at atmospheric pressure prior to going into the field to minimize any chance of entrapped oxygen within the module.

The power modules may utilize the same scheme as proposed for the computing module, including fluid-exclusion. However, the battery-packs may be housed in each module within its own pressure enclosure, designed for operation in 125 psig differential pressure conditions. The sealed packs may be purged of all air, and have the contents replaced with nitrogen at atmospheric pressure prior to going into the field to minimize any chance of entrapped oxygen within the module.

The launching chamber is loaded with the system 10 module-train, sealed and is preferably purged of all air and the contents replaced with nitrogen or another inert gas at atmospheric pressure. It remains sealed until the system 10 is deployed in the field. Once mounted atop the launch-valve-head assembly, the pressures between the launch-chamber and the main can be equalized manually, avoiding leaving entrapped air in the launch-sequence. The use of an inert gas, such as nitrogen, in the launch-chamber can be avoided, if shown that pressure-equalization and temporary bleeding of the same out the top of the launch-chamber, accomplishes the same goal—removal of air to the extent that the explosive-range environment is avoided prior to system power-up.

The operator-interface is fairly simple. The operator is presented, for example by means of the display screen of FIG. 25, with an image of the raw wide-angle-view of either the front/rear camera (or both at half the update-rate), have an estimated odometer-reading of total distance traveled, and indication of horizontal and vertical distance driven, current angles and estimated headings (based on operator determination and input of data regarding turn-angles taken in known places such as 90 and 45° turns), an overall indication of battery-charge status, and a bar-graph of the 'quality' (as expressed in data-throughput) of the wireless radio-link. The image generated by the camera may be forwarded to a second desktop computer for processing, allowing it to be dewarped, mosaiqued and stored to a local VHS-recorder or digital tape or the upcoming rewritable optical discs. The separation of the real-time operator control functions from the data-handling and processing as well as recording may be employed.

An alternative user interface may be in the form of a portable control box. The control box consists of a rugged plastic case. Its purpose is to display and control the picture taken by the camera inside the pipe. The box hooks up to 110 $V_{AC}$, one main switch controls the power supply of all electrical parts in the box and in the module. In the bottom part, there are separate power supplies (with isolated grounds) for the screen ($12V_{DC}$), for the camera and the lights (24VDC) and for the video amplifier board ($9V_{DC}$). There is an additional board to facilitate the connections between all internal electronic parts. There are two BNC video outputs for the output of the image data on external screens. Two trim potentiometers serve for the regulation of the light's brightness to optimize the picture (near and far lights can be changed separately). The cable coming from the camera module is connected with an Amphenol 20-pin connector—only 6 of the total 20 contacts are used. The video signal is transmitted over a coaxial cable (GND & $V_{out}$), two wires power up the camera (GND & $V_{cam}$) and two wires connect to the lights ($V_{near}$ & $V_{far}$)—the lights use the same ground as the camera power. To visualize the results, i.e., the picture of the gas pipes' inside, there is an 11.3" TFT-LCD monitor from, for example, Earth Computer Technologies placed in the lid of the case.

The operational scenario may be, for example, as detailed below. The main steps involve the establishment of the access-port for the system 10 robot, and then the subsequent launching and retrieval of the unit are detailed below in the conceived operations-log for the first field-day:

| DAY | TIME | STEP | ACTIVITY | COMMENTS |
|---|---|---|---|---|
| 1 | | Perimeter Establishment | Traffic Control Signs up | |
| | | | Lay out job & talk to crew | |
| | | Dig Hole | Emplace Excavator & Dig | |
| | | | Haul Dirt and Clean Area | |
| | | Fitting Installation | Clean Pipe | |
| | | | Weld-on Access Fitting | |
| | | | Install Gate-Valve | |
| | | Accessing Pipe | Install Drill-Jig | |
| | | | Drill Access Hole | |
| | | | Remove Drill-jig | |
| | | Ready Launch-System | Evacuate & Purge Launcher | |
| | | | Test system on truck | |
| | | Install Launch System | Hook, lower bolt chamber | |
| | | | Equalize Pressures | |
| | | Self-check of Inspection system 10 | Boot-up robot sequence | |
| | | | Open gate-valve | |
| | | | Test driving sequence | |
| | | | Re-dock system | |
| | | Shutdown | Close gate-valve & vent launch-chamber | |
| | | | Shutdown for next day launch | |

The operational scenario for the unit once the system has been installed are detailed below in the conceived operational-log for the second field-day:

| DAY | TIME | STEP | ACTIVITY | COMMENTS |
|---|---|---|---|---|
| 2 | | Launch Preparations | Vent, evacuate & purge chamber<br>Equalize Pressures<br>Open gate-valve | |
| | | System Wake-up | Inspection system 10 Start-up<br>System check-out | |
| | | Inspection system 10 Launch | Inspection system 10 Launch-Chamber Egress | |
| | | Mission Start-up | Inspection system 10 Travel begins<br>Inspection system 10 traversing network<br>System stand-by mode | Total Distance covered:<br>3,712 one-way feet |
| | | Mission Resumption | Inspection system 10 system wake-up<br>Inspection system 10 travel resumes<br>Inspection system 10 traversing network | Total Distance covered:<br>2,025 one-way feet |
| | | Round-Trip Session | Point-of-no-return notification<br>Reversing Inspection system 10 traverse | Total Distance covered:<br>5,737 return-way feet |
| | | System Extrication | Inspection system 10 arrival at launch chamber<br>Inspection system 10 self-driven extrication<br>Into chamber<br>Inspection system 10 docking and shutdown<br>Closing gate-valve<br>Venting launch-chamber<br>Power recharge circuit engagement | |
| | | Shutdown | System shutdown | |

The system will have covered a total one-way distance of 5,740 feet (~1.1 miles), allowing to return to a state within the launch-chamber, from which it could be re-launched the next day to cover an equivalent distance in the opposite direction, prior to removing the system, disconnecting the launch-chamber and restoring the launch-area.

The power cells in the power modules 14 of the system 10 have to be recharged periodically. One method of recharging, is to have the module train return to the launch point to a recharging station, which can be a generator, a transformer, a vehicle battery or any suitable power source of 24 volt DC and 2 amps. This method would involve making sure the module train returns to the recharging station before the on-board power supply is exhausted.

An alternative method of recharging includes installing recharge ports, spaced at intervals from each other along the pipeline. These may be permanent ports along the pipeline leading to a location external to the pipe. As work is planned for a length of pipe, a portable power source or a contact line from the power source can be inserted into the port and accessed by the module train as needed. The drive module, for example, may include a charging contact, such contact 47 in the drive module of FIG. 2 as the interface between the recharging station and the power cells of the power module 12.

Another concept for recharging the system 10 is to utilize the gasflow itself as a kinetic energy source, and given the acceptance of a minor pressure-drop, one may use an in-line turbine, which when driven by the gasflow, can drive a generator, which in turn can be used to directly-power or trickle-charge the on-board battery pack(s).

As part of the turbine use, there will be a pressure-drop across the turbine, due to two reasons: (i) power-extracted from the flow, and (2) head-loss due to the contraction and expansion of the gas through the turbine throat. It is known that turbines are typically not overly efficient at extracting power from flow, with efficiencies of around 30% being typical. Since the throat diameter is the most significant factor effecting pressure drop in the turbine, it is desirable to keep it as large as possible, but without affecting the systems' ability to pass protruding obstacles (taps). It was determined that the desirable 0.3 psig drop could be achieved by fully shaping the entry/exit path of the fluid-flow to minimize throat-construction pressure-drop.

The drive-modules may have integrated into their front ends, a way to allow the recharge and launch-chamber hook to grab the module and hold it, while allowing for active recharging of the battery-packs, even under complete power-drain conditions. This port may be configured to be orientation independent and safe to operate under all conditions.

The system 10 permits teleoperated long-range untethered, preferably video-inspection of live distribution gas mains. The system provides a 'crawler' system for live gas main access with wireless video & data communications utilizing on-board power sources. The system can traverse 2,500+ feet of standard 6- to 8-inch inside diameter piping, and can crawl through elbows, mitered joints, Ts, climb and descend inclined and vertical sections, while safely operating in a medium-to-high pressure pure natural gas environment, allowing operators to communicate and receive live video in real time, including accurate navigation position-estimates.

The system of the present invention is well suited for use by the gas utilities in distribution mains, typically ranging in size from 6 to 8 inches internal diameter. The inspection system 10 of the present invention is believed to be far simpler and cheaper to build, deploy and operate than systems heretofore available, and provides live video feedback at complete power-autonomy and at a higher speed, range and duration than is currently possible with tethered systems. Those skilled in the art will recognize that the system 10 of the present invention can be adapted for use in other remote locations. The modules of the system 10 may also include specialized funtions or specialized modules interposed within the mid-train modules for specific activities, such as repairing sections of pipe.

The use of untethered inspection systems is expected to radically improve gas line inspection and repair. Since the system is insensitive to which material the pipe is made of, it is applicable to almost 100% of pipelines. Possible savings are hard to estimate, but if one assumes that up to 50% of the currently section-replaced/relined or completely pipelines could have been repaired with the next-'cheapest' repair method, savings may be on the order of 25% to 50% over conventional replacement techniques, saving the gas industry tens of millions of dollars annually. The inspection system 10 varies from existing systems because it is not limited by the length of a hard-connection to the outside (e.g., a tether or pushrod) that can be dragged or pushed down a pipe. Hence, the ability to provide power from on-board and to wirelessly communicate imagery and data to a remote location outside of the pipe open up a whole new realm of possibilities.

What is claimed is:

1. A system for inspection of selective conditions in a pipeline comprising:
    a self-propelled train comprising:
        a plurality of modules, at least one of said modules having a drive mechanism for effecting locomotion of said train;
        at least one joint member for interconnecting adjacent modules in said train, said joint member configured to allow articulation of said modules relative to each other through multiple planes and angles;
        data collection components; and,
        communication components for transmitting collected data;
    wherein said plurality of modules further comprises:
    two terminal modules, one positioned at each end of the train, and a plurality of mid train modules positioned between the terminal modules;
    wherein the at least one joint members of the system further comprise:
    a double-axis steerable interconnect joint positioned between each terminal module and the mid-train module adjacent thereto, said double-axis interconnect joint being movable about two axes of rotation;
    a single-axis steerable interconnect joint positioned between adjacent mid-train modules, said single-axis interconnect joint being movable about a single axis or rotation;
    each of said double-axis interconnect joints rotate about both a pitch axis and a roll axis, and each of said single-axis interconnect joints rotate about a pitch axis;
    wherein said modules each comprise a motor for driving the movement of said double-axis and single-axis interconnect joints;
    wherein each of said double-axis and single-axis interconnect joints include a rotatable gear mounted on each module of the joint for engagement with the rotatable gear on the adjacent module;
    wherein each module has a central axis and the motor in each said terminal modules is offset from the central axis of that module and each terminal module comprises:
        a first mounting member positioned on an end of said terminal module adjacent one of said mid-train modules;
        one of said rotatable gears; and,
        a first gear assembly driven by the motor for imparting rotation to said rotatable gear.

2. The system of claim 1 wherein said plurality of modules include at least one drive module.

3. The system of claim 2 wherein said drive module includes said drive mechanism, which further comprises:
    a motor assembly;
    a drive shaft operatively connected to and driven by said motor assembly;
    a plurality of drive arms, each drive arm having at least one driven wheel rotatably attached at a free end of said drive arm; and,
    a gear assembly for translating movement of said drive shaft to said driven wheels to effect locomotion of said train.

4. The system of claim 3 wherein said drive mechanism further comprises:
    an extension shaft operatively connected to and driven by said motor assembly;
    a linkage assembly operatively connected to said extension shaft and to each of said plurality of drive arms for extending and collapsing said drive arms relative to said drive module.

5. The system of claim 4 wherein said linkage assembly comprises:
    a plurality of extension arms, each extension arm pivotally connected to a different one of said drive arms; and,
    an extension unit pivotally connected to each of said extension arms and operatively connected to said extension shaft for translating movement of said extension shaft to said extension arms.

6. The system of claim 4 wherein said motor assembly comprises:
    a drive motor for driving said drive shaft; and,
    an extension motor for driving said extension shaft.

7. The system of claim 2 wherein said data collection components are housed in said drive module and comprise a camera and lights.

8. The system of claim 1 wherein said data collection components are selected from the group consisting of imaging systems including a camera and light source, ultasonic wall thickness sensors, potentiometers, accelerometers, sensors for detecting magnetic flux leakage, sensors for detecting eddy currents, wheel follower odometers and any combination thereof.

9. The system of claim 1 wherein said plurality of modules include at least one power module.

10. The system of claim 30 wherein said power source is rechargeable by generating power with an in line gas flow powered turbine system.

11. The system of claim 1 wherein the mid-train modules adjacent said terminal modules comprise:
   a second mounting member positioned on an end of said mid-train module adjacent said terminal module, said second mounting member being rotatable about the central axis of the mid-train module on which it is positioned; and,
   one of said rotatable gears positioned on said second mounting member in an orientation such that the axis of its rotation is perpendicular to the axis of rotation of said second mounting member and perpendicular to the axis of rotation of said rotatable gear of said terminal module.

12. The system of claim 9 wherein said power module comprises:
   a power source; and,
   means for transferring power from said power source to each of said drive mechanism, said data collection components and said data communication components.

13. The system of claim 10 wherein said turbine system comprises:
   an in-line turbine driven by gas flow within the pipeline; and,
   a generator driven by the turbine for supplying energy to said power source.

14. The system of claim 11 wherein said first mounting member comprises:
   a pair of opposing clevis mounts spaced from each other;
   said rotatable gear of said terminal module being positioned for rotation about an axis of rotation between said opposing clevis mounts; and,
   said second mounting member being pivotally connected to said pair of opposing clevis mount.

15. The system of claim 12 wherein said power source is rechargeable.

16. The system of claim 12 wherein the pipeline includes a portal to a location external to the pipe and said power source is rechargeable by connection through the portal to a generator external to the pipeline.

17. The system of claim 12 wherein said power source comprises a chemical energy source.

18. The system of claim 17 wherein said chemical energy source is a battery pack.

19. The system of claim 18 wherein said battery pack is comprised of at least two sub packs, each having a plurality of battery cells therein.

20. The system of claim 19 wherein said battery cells are selected from the group consisting of lithium ion cells, nickel metal hydride cells and alkaline cells.

21. A system for inspection of selective conditions in a pipeline comprising:
   a self-propelled train comprising:
      a plurality of modules, at least one of said modules having a drive mechanism for effecting locomotion of said train;
      at least one joint member for interconnecting adjacent modules in said train, said joint member configured to allow articulation of said modules relative to each other through multiple planes and angles, said at least one joint member comprising a double-axis steerable interconnect joint comprised of a first interconnect unit positioned on one of said modules and rotatably and pivotally connected to a second interconnect unit positioned on an adjacent one of said modules and a single-axis steerable interconnect joint comprised of a third interconnect unit positioned on one of said modules and rotatably connected to a fourth interconnect unit positioned on an adjacent one of said modules, said modules interconnected by said single-axis interconnect joint having no more than one module in common with said modules interconnected by said double-axis interconnect joint;
      data collection components; and,
      communication components for transmitting collected data.

22. The system of claim 21 wherein said data collection components comprise an imaging system.

23. The system of claim 21 wherein said data collection components are selected from the group consisting of imaging systems including a camera and light source, ultrasonic wall thickness sensors, potentiometers accelerometers, sensors for detecting magnetic flux leakage, sensors for detecting eddy currents, wheel follower odometers and any combination thereof.

24. The system of claim 21 further comprising:
   a power source, wherein said power source is rechargeable by generating power with an in-line gas flow powered turbine system, said turbine system comprising;
   an in-line turbine driven by gas flow within the pipeline; and,
   a generator driven by the turbine for supplying energy to said power source.

25. The system of claim 21 wherein each said module has a central axis and each of said third and fourth interconnect units comprises:
   a single-axis mounting member positioned on an end of a module in facing relationship to an end of an adjacent module;
   a third motor assembly;
   a third gear assembly operatively connected to said third motor assembly; and,
   a portion of said third gear assembly positioned for rotation about an axis of rotation.

26. The system of claim 25 wherein said single axis mounting members are fixedly attached to their respective modules;
   said axis of rotation of said gear portion of said third interconnect unit is substantially parallel to the central axis of the module on which said third interconnect unit is positioned; and,
   said axis of rotation of said gear portion of said fourth interconnect unit is offset from the central axis of the module on which said fourth interconnect unit is positioned by about ninety degrees.

27. The system of claim 26 wherein said third gear assemblies each include a pinion-bevel gear.

28. The system of claim 21 wherein said plurality of modules further comprises:
   at least one drive module positioned on the end of said train;
   at least two power modules, one being positioned adjacent to each drive module; and,
   said double-axis interconnect joint is positioned between each said drive module and said power module adjacent to said drive module.

29. The system of claim 21 wherein said communication components comprise wireless communication components.

30. The system of claim 29 wherein said wireless communication components comprise an antenna for communicating to a remote receiver.

31. The system of claim 30 wherein said antenna comprises an inverted F antenna and antenna reflector circuit board.

32. The system of claim 29 wherein said wireless communication components comprise a wireless Ethernet link to a remote receiver.

33. The system of claim 29 wherein said wireless communication components comprise means for transmitting low frequency electromagnetic waves through one or both of the pipe and the pipe walls.

34. The system of claim 27 wherein said wireless communication components comprise means for transmitting radio-waves.

35. The system of claim 21 wherein said communication components comprise fiber optic cables having an optical communications link.

36. The system of claim 21 wherein said plurality of modules include at least one support module.

37. The system of claim 36 wherein said support module comprises:
a support arm mechanism for supporting said train.

38. The system of claim 22, wherein:
a first of the plurality of modules includes the imaging system; and
a second of the plurality of modules includes a digital image receiver in communication with the imaging system for receiving image data captured by the imaging system.

39. The system of claim 38, wherein the digital image receiver includes a LVDS receiver.

40. The system of claim 38 wherein the second module further includes a processor in communication with the digital image receiver for processing the image data.

41. The system of claim 38, wherein the second module further comprises wireless network communications components in communication with the processor.

42. The system of claim 41, wherein:
the processor is for packetizing the image data; and
the wireless network communications components are for transmitting the packetized image data via a wireless communication network to a remote user interface.

43. A system for inspection of selective conditions in a pipeline comprising:
a self-propelled train comprising:
a plurality of modules, at least one of said modules having a drive mechanism for effecting locomotion of said train;
at least one joint member for interconnecting adjacent modules in said train, said joint member configured to allow articulation of said modules relative to each other through multiple planes and angles, said at least one joint member comprising a double-axis steerable interconnect joint comprised of a first interconnect unit positioned on one of said modules and rotatably and pivotally connected to a second interconnect unit positioned on an adjacent one of said modules and
wherein said a first interconnect unit comprises:
a first mounting member positioned on an end of a module in facing relationship to an end of an adjacent module;
a first steering motor assembly;
a first gear assembly operatively connected to said first steering motor assembly; and,
a portion of said first gear assembly positioned for rotation about a first axis of rotation.

44. The system of claim 43 wherein said first mounting member comprises a pair of clevis mounts defining a space therebetween and said portion of said first gear is positioned in said space between said pair of clevis mounts.

45. The system of claim 43 wherein each said module has a central axis and said first mounting member comprises a swivel block rotatable about an axis of rotation parallel to the central axis of the module on which said swivel block is positioned and said first axis of rotation is offset about ninety degrees relative to the axis of rotation of said swivel block.

46. The system of claim 43 wherein said second interconnect unit comprises:
a second mounting member positioned on an end of a module in facing relationship to an end of an adjacent module;
a second steering motor assembly;
a second gear assembly operatively connected to said second steering motor assembly; and,
a portion of said second gear assembly positioned for rotation about a second axis of rotation.

47. The system of claim 46 wherein said second mounting member comprises a pair of clevis mounts defining a space therebetween and said portion of said second gear is positioned in said space between said pair of clevis mounts.

48. The system of claim 46 wherein each said module has a central axis;
said second mounting member on said second interconnect unit comprises a swivel block rotatable about an axis of rotation parallel to the central axis of the module on which said swivel block is positioned; and,
said second axis of rotation is offset about ninety degrees relative to the axis of rotation of said swivel block.

49. The system of claim 48 wherein said first mounting member on said first interconnect unit comprises a pair of clevis mounts defining a space therebetween and said portion of said first gear is positioned in said space between said pair of clevis mount;
said swivel block is pivotally connected to said pair of clevis mounts; and,
the first axis of rotation is substantially parallel to the central axis of the module on which said first interconnect unit is positioned and is substantially perpendicular to the second axis of rotation.

50. The system of claim 43 wherein said plurality of modules comprise:
two drive modules, one positioned at each end of said train;
two power modules, each power module being positioned adjacent to a different one of said drive modules; and,
two support modules, each support module being positioned adjacent to a different one of said power modules; and,
an electronics module positioned between said two support modules.

51. The system of claim 50 wherein each said power module comprises:
a power source; and,
means for transferring power from said power source to each of said drive mechanism, said data collection components and said data communication components.

52. The system of claim 51 wherein said power source is rechargeable.

53. The system of claim 52 wherein said power source is rechargeable by generating power with an in line gas flow powered turbine system.

54. The system of claim 52 wherein said power source is rechargeable by electrical connection to a generator.

55. The system of claim 51 wherein said power source comprises a chemical energy source.

56. The system of claim 55 wherein said chemical energy source is a battery pack.

57. The system of claim 50 wherein each said support module comprises:
 a housing having first and second end caps;
 a support arm mechanism positioned within said housing of said support module for supporting said train; and,
 electronic components for communication of electrical signals to and from said support module to at least one other module within said train.

58. The system of claim 50 wherein said electronics module includes computer components comprising a processor and a converter, and electrical connection members for passage of electrical signals between said electronics module and at least one other module of said plurality of modules.

59. The system of claim 43 wherein said plurality of modules includes two drive modules positioned at each end of said train, and an electronics module positioned therebetween; each said drive module having one of said drive mechanisms and said data collection components housed therein, and said electronics module having a power supply and computing components housed therein.

60. The system of claim 43 wherein said plurality of modules includes two drive modules positioned at each end of said train, each said drive module having one of said drive mechanisms and said data collection components housed therein, and a power module positioned between said drive modules, said power module having a battery pack and computing components housed therein, said battery pack having sufficient stored power for providing power to drive said drive mechanisms, said data collection components, said wireless communication components and said computing components for at least eight hours of continuous operation.

61. The system of claim 60 wherein said data collection components are selected from the group consisting of imaging systems including a camera and light source, potentiometers accelerometers, sensors for detecting magnetic flux leakage, sensors for detecting eddy currents, ultrasonic sensors, wheel follower odometers and any combination thereof.

62. A system for inspection of selective conditions in a pipeline comprising:
 a self-propelled train comprising:
  a plurality of modules comprising at least one support module having a support arm mechanism for supporting said train, and at least one of said plurality of modules having a drive mechanism for effecting locomotion of said train;
  at least one joint member for interconnecting adjacent modules in said train, said joint member configured to allow articulation of said modules relative to each other through multiple planes and angles;
  data collection components; and,
  communication components for transmitting collected data;
 wherein said support arm mechanism comprises:
  a plurality of passive arms, each said passive arm having a wheel rotatably attached to a free end thereof; and,
  an idler motor assembly;
  an extension shaft operatively connected to and driven by said idler motor assembly;
  a linkage assembly operatively connected to said extension shaft and to each of said plurality of passive arms for extending and collapsing said passive arms relative to said support module for supporting and centering said train within the pipeline as the train moves.

63. The system of claim 62 wherein said data collection components are selected from the group consisting of imaging systems including a camera and light source, ultraconic wall thickness sensors potentiometers, accelerometers, sensors for detecting magnetic flux leakage, sensors for detecting eddy currents, wheel follower odometers and any combination thereof.

64. The system of claim 62 wherein said at least one joint member comprises a universal joint.

65. The system of claim 62 wherein each module of said train has a central axis and at least one of said joint members is configured for rotation about a first axis generally perpendicular to the central axis of the module to which the joint member is interconnected and for rotation about a second axis generally parallel to the central line of the module to which the joint member is interconnected.

66. The system of claim 62 wherein said plurality of modules further comprises:
 two terminal modules, one positioned at each end of the train;
 a plurality of mid train modules including said support modure positioned between the terminal modules, and,
 wherein there are multiple joint members of the system further comprising:
 a double-axis steerable interconnect joint positioned between each terminal module and the mid-train module adjacent thereto, said double-axis interconnect joint being movable about two axes of rotation;
 a single-axis steerable interconnect joint positioned between adjacent mid-train modules, said single-axis interconnect joint being movable about a single axis or rotation.

67. The system of claim 66 wherein each of said double-axis interconnect joints rotate about both a pitch axis and a roll axis, and each of said single-axis interconnect joints rotate about a pitch axis.

68. The system of claim 67 wherein said modules each comprise a motor for driving the movement of said double-axis and single-axis interconnect joints.

69. The system of claim 68 wherein each of said double-axis and single-axis interconnect joints include a rotatable gear mounted on each module of the joint for engagement with the rotatable gear on the adjacent module.

70. The system of claim 62 wherein said linkage assembly comprises:
 a plurality of idler extension arms, each idler extension arm pivotally connected to a different one of said passive arms; and,
 a nut pivotally connected to each of said idler extension arms and operatively connected to said extension shaft for translating movement of said extension shaft to said passive arms.

71. The system of claim 62 wherein said passive arms carry motion sensors for detecting the rotational movements of said wheels of said passive arms.

72. The system of claim 62 wherein there are at least two passive arms spaced from each other about said support module.

73. The system of claim 62 wherein said support module further comprises at least one interconnect unit on an end thereof for interconnection to an adjacent one of said plurality of modules.

74. The system of claim 62 wherein said plurality of modules comprises:
- at least one drive module positioned at an end of said train, said at least one drive module having said drive mechanism and said data collection components housed therein;
- at least one power module positioned adjacent to one end of said at least one drive module, said at least one power module having a battery pack; and,
- an electronics module positioned adjacent one of said drive module and said power module, said electronics module having computing components housed therein,
- wherein said battery pack has sufficient stored power for providing power to drive said drive mechanisms, said data collection components, said wireless communication components and said computing components for at least eight hours of continuous operation.

75. The system of claim 74 further comprising sensors in said power module.

76. The system of claim 74 further comprising sensors in said electronics module.

77. The system of claim 74 wherein said joint members interconnecting each of said adjacent modules comprise universal joints.

78. The system of claim 74 wherein said data collection components are selected from the group consisting of imaging systems including a camera and light source, potentiometers, accelerometers, sensors for detecting magnetic flux leakage, sensors for detecting eddy currents, wheel follower odometers and any combination thereof.

79. A system for inspection of selective conditions in a pipeline comprising:
- a self-propelled train comprising:
  - a plurality of modules comprising at least one support module having at least one interconnect unit on an end thereof for interconnection to an adjacent one of said plurality of modules and at least one of said plurality of modules having a drive mechanism for effecting locomotion of said train;
  - at least one joint member for interconnecting adjacent modules in said train, said joint member configured to allow articulation of said modules relative to each other through multiple planes and angles;
  - data collection components; and,
  - communication components for transmitting collected data;
- wherein said interconnect unit comprises:
  - a pair of opposing clevis mounts spaced from each other;
  - a steering motor assembly;
  - a first gear assembly operatively connected to said steering motor assembly; and,
  - a portion said first gear assembly positioned for rotation about a single axis of rotation between the pair of clevis mounts.

80. The system of claim 79 further comprising:
- a power source;
- an in-line turbine driven by gas flow within the pipeline; and,
- a generator driven by the turbine for supplying energy to said power source.

81. The system of claim 79 wherein said data collection components are selected from the group consisting of imaging systems including a camera and light source, ultraconic wall thickness sensors, potentiometers, accelerometers, sensors for detecting magnetic flux leakage, sensors for detecting eddy currents, wheel follower odometers and any combination thereof.

82. The system of claim 79 wherein said support module has two interconnect units, one on each end thereof, said interconnect units being movable about a single axis of rotation.

83. The system of claim 79 wherein said support module includes electrical connection members for passage of electrical signals between at least one other module of said plurality of modules.

84. The system of claim 79 wherein said plurality of modules includes an electronics module.

85. The system of claim 84 wherein said electronics module includes computer components.

86. The system of claim 85 wherein said computer components comprise a processor and a converter, and electrical connection members for passage of electrical signals between said electronics module and at least one other module of said plurality of modules.

87. The system of claim 84 wherein said electronics module includes a portion of a joint member, said portion comprising at least one single axis interconnect unit for interconnecting said electronics module to an adjacent one of said plurality of modules.

88. A system for inspection of selective conditions in a pipeline comprising:
- a self-propelled train comprising:
  - a plurality of modules comprising an electronics module, said electronics module including a portion of a joint member, said portion comprising at least one single axis interconnect unit for interconnecting said electronics module to an adjacent one of said plurality of modules; at least one of said plurality of modules having a drive mechanism for effecting locomotion of said train;
  - at least one joint member for interconnecting adjacent modules in said train, said joint member configured to allow articulation of said modules relative to each other through multiple planes and angles;
  - data collection components; and,
  - communication components for transmitting collected data said one single axis interconnect unit comprises:
  - a mounting unit configured for pivotally connecting to a pair of clevis mounts of said adjacent module; and,
  - a gear assembly mounted for rotation on said mounting unit about an axis of rotation;
  - said gear assembly having a portion thereof configured for complementary rotational engagement with a gear assembly on said adjacent module.

89. The system of claim 88 wherein said plurality of modules further comprises:
- a leading drive module;
- a power module;
- a first one of said plurality of joint members connecting one end of said leading drive module to one end of said power module, said power module having another end;
- a support module;
- a second one of said plurality of joint members connecting said other end of said power module to said support module, said support module having another end;
- wherein said electronics module is connected to said other end of said support module by a third one of said plurality of joint members and said single axis interconnect unit on said electronics module forms a portion of the third joint member connecting said electronics module to said support module.

90. The system of claim 89 wherein each said module of said plurality of modules has a central axis and said first one of said plurality of joint members comprises a joint configured for rotation about a first axis generally perpendicular to the central axis of the drive module and for rotation about a second axis generally parallel to the central line of the drive module; and, said second one of said plurality of joint members comprises a joint configured for rotation about an axis generally perpendicular to the central axis of at least one of the power module or the support module.

91. The system of claim 90 wherein said first one of said plurality of joint members first and second interconnect units, said first interconnect unit comprising:

a pair of opposing clevis mounts defining a space therebetween;

a steering motor assembly;

a first gear assembly operatively connected to said steering motor assembly; and, a portion said first gear assembly positioned for rotation about an axis of rotation between the pair of clevis mounts and having an engagement surface.

92. The system of claim 91 wherein said leading drive module includes said first interconnect unit;

said adjacent power module includes a mounting member positioned on an end of thereof for rotation about the central axis of said power module and a rotatable gear positioned on said mounting member in an orientation such that the axis of rotation of said power module gear is perpendicular to the axis of rotation of said portion of said first gear assembly of said drive module, said power module gear having an engagement surface thereon configured for complementary engagement with the engagement surface of said portion of said first gear.

93. The system of claim 92 wherein said support module includes one of said second one of said plurality of joint members on each end thereof.

94. The system of claim 93 further comprising;

two drive modules, one positioned at each end of said train;

two power modules, each being positioned adjacent to a different one of said drive modules; and, two support modules, each being positioned adjacent to a different one of said power modules;

wherein said electronics module is positioned between said support modules.

95. A system for inspection of selective conditions in a pipeline comprising:

a self-propelled train comprising:
 a plurality of modules, at least one of said modules having a drive mechanism for effecting locomotion of said train;
 at least one joint member for interconnecting adjacent modules in said train, said joint member configured to allow articulation of said modules relative to each other through multiple planes and angles;
 data collection components; and,
 communication components for transmitting collected data;
wherein said plurality of modules comprise:
two drive modules, one positioned at each end of said train;
two power modules, each power module being positioned adjacent to a different one of said drive modules; and, two support modules, each support module being positioned adjacent to a different one of said power modules; and, an electronics module positioned between said two support modules; and, wherein one of said plurality of joint members is positioned between each said drive module and an adjacent said power module, said joint member comprising a drive interconnect unit and a power interconnect unit, said drive interconnect unit comprising:

a pair of opposing clevis mounts spaced from each other;

a steering motor assembly;

a first gear assembly operatively connected to said steering motor assembly; and, a portion said first gear assembly positioned for rotation about an axis of rotation between the pair of clevis mounts.

96. The system of claim 95 wherein each said module has a central axis and each of said power interconnect units comprises:

a mounting unit mounted for rotation about the central axis of the power module and pivotally connected to said pair of clevis mounts of said adjacent drive interconnect unit;

a second gear assembly mounted for rotation on said mounting unit about an axis off set from the axis of rotation of said first gear assembly by about 90°;

said second gear assembly having a portion thereof configured for complementary rotational engagement with said portion of said first gear assembly.

97. The system of claim 96 wherein said drive modules comprise:

a housing having a front end cap and a rear end cap;

said drive mechanism poisoned in said housing;

said data collection components positioned in said front end cap; and, said wireless communication components positioned in said housing.

98. The system of claim 97 wherein said drive mechanism comprises:

a motor assembly;

a drive shaft operatively connected to and driven by said motor assembly;

a plurality of drive arms extending outwardly from said housing, each drive arm having at least one driven wheel rotatably attached at a free end of said drive arm external to said housing of said drive member; and, a gear assembly for translating movement of said drive shaft to said driven wheels to effect locomotion of said train.

99. The system of claim 98 wherein said drive mechanism further comprises:

an extension shaft operatively connected to and driven by said motor assembly;

a linkage assembly operatively connected to said extension shaft and to each of said plurality of drive arms for extending said drive arms outwardly from said housing of said drive module and collapsing said drive arms into said housing of said drive module.

100. The system of claim 99 wherein said linkage assembly comprises:

a plurality of extension arms, each extension arm pivotally connected to a different one of said drive arms; and, an extension unit pivotally connected to each of said extension arms and operatively connected to said extension shaft for translating movement of said extension shaft to said extension arms.

101. The system of claim 100 wherein there are at least two drive arms radially spaced from each other.

102. The system of claim 101 wherein said motor assembly comprises:
a drive motor for driving said drive shaft; and,
an extension motor for driving said extension shaft.

103. The system of claim 97 wherein said data collection components comprise an imaging system.

104. The system of claim 103 wherein said imaging system comprises a camera and lights.

105. A system for inspection of selective conditions in a pipeline comprising:
a self-propelled train comprising:
data collection components;
communication components for transmitting collected data;
a plurality of modules, comprising
two drive modules, one positioned at each end of said train for effecting locomotion of said train;
two power modules, each power module being positioned adjacent to a different one of said drive modules;
two support modules, each support module being positioned adjacent to a different one of said power modules, and each said support module having a housing having first and second end caps, a support arm mechanism positioned within said housing of said support module for supporting said train, and electronic components for communication of electrical signals to and from said support module to at least one other module within said train; and,
an electronics module positioned between said two support modules,
at least one joint member for interconnecting adjacent modules in said train, said joint member configured to allow articulation of said modules relative to each other through multiple planes and angles;
wherein said support arm mechanism comprises:
a plurality of passive arms, each said passive arm having a wheel rotatably attached to a free end thereof;
an idler motor assembly in said support module housing;
an extension shaft in said support module housing operatively connected to and driven by said idler motor assembly; and,
a linkage assembly operatively connected to said extension shaft and to each of said plurality of passive arms for extending said passive arms outwardly from said support module housing and collapsing said passive arms into said support module housing.

106. The system of claim 105 wherein said linkage assembly comprises:
a plurality of idler extension arms, each idler extension arm pivotally connected to a different one of said passive arms; and,
a nut pivotally connected to each of said idler extension arms and operatively connected to said extension shaft for translating movement of said extension shaft to said passive arms.

107. The system of claim 105 wherein said passive arms carry locomotion sensors for detecting the rotational movements of said wheels of said passive arms.

108. The system of claim 105 wherein there are at least two passive arms spaced radially from each other about said support module housing.

* * * * *

UNITED STATES PATENT AND TRADEMARK OFFICE
CERTIFICATE OF CORRECTION

PATENT NO. : 6,917,176 B2
DATED : July 12, 2005
INVENTOR(S) : Hagen Schempf, Edward Mutschler and Vitaly Goltsberg It is certified that error appears in the above-identified patent and that said Letters Patent is hereby corrected as shown below:

Column 1,
Line 6, insert the following:
-- This invention was made with support from the National Aeronautical and Space Administration. The United States Government has certain rights in the invention. --.

Column 9,
Line 57, delete "devises" and substitute therewith -- clevises --.

Column 10,
Line 56, delete "devises" and substitute therewith -- clevises --.

Column 11,
Line 9, delete "devises" and substitute therewith -- clevises --.

Signed and Sealed this

Fifteenth Day of November, 2005

JON W. DUDAS
*Director of the United States Patent and Trademark Office*